United States Patent
Ohashi et al.

(10) Patent No.: US 11,090,403 B2
(45) Date of Patent: Aug. 17, 2021

(54) POROUS SILICA AND DEODORANT COMPRISING THE SAME

(71) Applicant: Toyo Seikan Group Holdings, Ltd., Tokyo (JP)

(72) Inventors: Kazuaki Ohashi, Yokohama (JP); Mariko Kimura, Yokohama (JP)

(73) Assignee: TOYO SEIKAN GROUP HOLDINGS, LTD., Tokyo (JP)

( * ) Notice: Subject to any disclaimer, the term of this patent is extended or adjusted under 35 U.S.C. 154(b) by 0 days.

(21) Appl. No.: 15/745,244

(22) PCT Filed: Jul. 15, 2016

(86) PCT No.: PCT/JP2016/070996
§ 371 (c)(1),
(2) Date: Jan. 16, 2018

(87) PCT Pub. No.: WO2017/014186
PCT Pub. Date: Jan. 26, 2017

(65) Prior Publication Data
US 2019/0001014 A1    Jan. 3, 2019

(30) Foreign Application Priority Data

Jul. 17, 2015 (JP) ................................. 2015-143278
Jan. 21, 2016 (JP) ................................. 2016-009948
Jan. 21, 2016 (JP) ............................. JP2016-009949

(51) Int. Cl.
| | | |
|---|---|---|
| *A61K 6/84* | (2020.01) | |
| *A61K 9/14* | (2006.01) | |
| *A01N 25/12* | (2006.01) | |
| *A61L 9/014* | (2006.01) | |
| *B01J 20/10* | (2006.01) | |
| *C01B 33/18* | (2006.01) | |
| *B01J 20/28* | (2006.01) | |
| *B01J 20/30* | (2006.01) | |
| *C01B 33/12* | (2006.01) | |
| *A61L 9/16* | (2006.01) | |
| *C01B 37/02* | (2006.01) | |
| *A61L 9/01* | (2006.01) | |
| *B01J 20/02* | (2006.01) | |

(52) U.S. Cl.
CPC ................. *A61L 9/014* (2013.01); *A61L 9/01* (2013.01); *A61L 9/16* (2013.01); *B01J 20/024* (2013.01); *B01J 20/0222* (2013.01); *B01J 20/0225* (2013.01); *B01J 20/0233* (2013.01); *B01J 20/0237* (2013.01); *B01J 20/10* (2013.01); *B01J 20/28* (2013.01); *B01J 20/28007* (2013.01); *B01J 20/28064* (2013.01); *B01J 20/28066* (2013.01); *B01J 20/30* (2013.01); *B01J 20/3078* (2013.01); *C01B 33/12* (2013.01); *C01B 33/18* (2013.01); *C01B 37/02* (2013.01); *A61L 2209/22* (2013.01); *C01P 2004/64* (2013.01); *C01P 2006/12* (2013.01)

(58) Field of Classification Search
CPC ............ C04B 38/0064; C04B 41/5096; C04B 38/0054; C04B 2235/428; C04B 38/0051; C04B 38/0096; A61K 9/5115; A61K 9/143; A61K 33/24; A61K 8/0279; A61K 8/26; A61K 9/51; A61K 2800/412; A61K 8/25; A61K 33/34; A61K 33/38; A61K 9/14; A61K 47/6923; A61Q 15/00; A61Q 19/00; A61Q 17/005
See application file for complete search history.

(56) References Cited

U.S. PATENT DOCUMENTS

| | | | | |
|---|---|---|---|---|
| 6,800,267 B2 * | 10/2004 | Schubert | ............... | B41M 5/5218 106/266 |
| 2003/0152759 A1 * | 8/2003 | Chao | .................... | B01J 29/0308 428/307.3 |
| 2009/0214606 A1 * | 8/2009 | Bujard | ................... | A01N 25/08 424/401 |
| 2013/0315972 A1 * | 11/2013 | Krasnow | ................ | A01N 25/12 424/409 |
| 2016/0052837 A1 | 2/2016 | Chen et al. | | |

FOREIGN PATENT DOCUMENTS

| | | | | |
|---|---|---|---|---|
| EP | 1151974 A2 * | 11/2001 | ......... | B01D 67/0069 |
| JP | H04313348 A | 11/1992 | | |
| JP | 2002187712 A | 7/2002 | | |
| JP | 2009249268 A | 10/2009 | | |
| JP | 2014043381 A | 3/2014 | | |
| WO | 2014/070116 A1 | 5/2014 | | |

OTHER PUBLICATIONS

Li, X., et al., "Synthesis of Titania-Doped Mesoporous Silica and its Gas Adsorbability", Journal of the Ceramic Society of Japan, 109 [10] 818-822 (2001).
International Search Report for PCT/JP2016/070996, dated Aug. 16, 2016.

* cited by examiner

Primary Examiner — Tracy Liu
(74) Attorney, Agent, or Firm — Hoffmann & Baron, LLP

(57) ABSTRACT

To provide a porous silica which is capable of effectively eliminating odors of methyl mercaptan, hydrogen sulfide, nonenal and the like, said odors being difficult to be eliminated by a silica porous material that contains no metal. A porous silica containing particles that are provided with primary pores, wherein the particles contain a metal containing substance complex having a particle size of 1-100 nm. This porous silica has a specific surface area of 500 m$^2$/g or more.

8 Claims, 11 Drawing Sheets

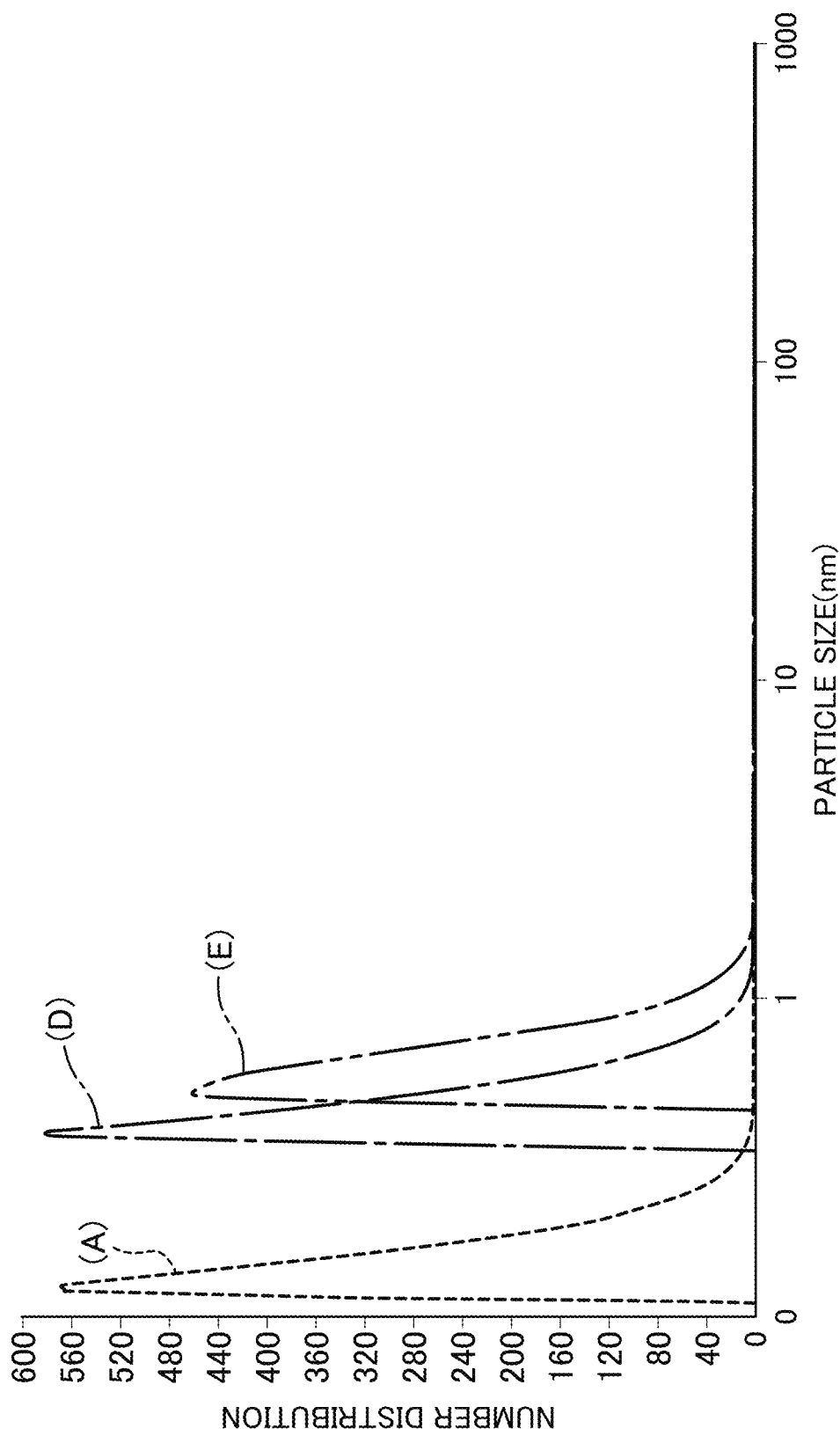

POROUS SILICA AND DEODORANT COMPRISING THE SAME

This application is the National Stage Entry under 35 U.S.C. § 371 of International Patent Application No. PCT/JP2016/070996, filed Jul. 15, 2016, which in turn claims priority to each of: (i) Japanese Patent Application No. 2015-143278, filed Jul. 17, 2015; (ii) Japanese Patent Application No. 2016-009948, filed Jan. 21, 2016; and (iii) Japanese Patent Application No. 2016-009949, filed Jan. 21, 2016. The contents of each of the foregoing applications are incorporated in their entirety by reference herein.

TECHNICAL FIELD

The present invention relates to a porous silica, a deodorant comprising the same, and a method for producing a porous silica. More specifically, the present invention relates to a porous silica which comprises a particle having a primary pore derived from a template, which has a large specific surface area due to inclusion of a secondary pore including a particle gap due to binding of the particles, and on which a metal-containing substance derived from a fatty acid metal salt introduced is supported.

BACKGROUND ART

Many studies have been reported about a metal-containing porous silica. For example, Xianying LI, Masato UEHARA, Naoya ENOMOTO, Junichi HOJO et al., "J. Ceram. Soc. Japan, 109, [10], 818-822 (2001)" describe (1) production of a porous material containing silica and titanium by dropping tetraethoxysilane and tetraethoxytitanium into a polyoxyethylene [23] lauryl ether aqueous solution to which hydrochloric acid is added, and (2) production of a porous material containing zinc oxide by mixing mesoporous silica and zinc nitrate and then calcining the mixture.

In addition, Japanese Patent Laid-Open No. 4-313348 describes a method for producing a supported catalyst of a metal or a metal oxide by immersing a carrier in an organic solution of an organometallic compound and supporting the organic compound on the carrier.

Furthermore, Japanese Patent Laid-Open No. 2002-187712 describes a method for producing a spherical porous silica or a silica metal composite particle, the method comprising adding water or an acidic aqueous solution to a mixed liquid including a water-miscible organic solvent, an alkyl amine and a silicic' acid ester or a combination of a silicic acid ester with a metal salt soluble in the water-miscible organic solvent, while stirring, to produce a silica-alkyl amine composite product, allowing the silica-alkyl amine composite product to grow into a spherical particle, and removing the alkyl amine in the spherical particle.

CITATION LIST

Patent Literature

Patent Literature 1: Japanese Patent Laid-Open No. 4-313348
Patent Literature 2: Japanese Patent Laid-Open No. 2002-187712

Non Patent Literature

[Non Patent Literature 1] Xianying Li et al., J. Ceram. Soc. Japan, 109, [10], 818-822 (2001)

SUMMARY OF INVENTION

Technical Problem

In introduction of a metal component other than Si during synthesis (Japanese Patent Laid-Open No. 2002-187712), a problem is that only a metal alkoxide, or a straight chain alkyl amine, or a limited metal salt soluble in water can be used in order to form a stable homogeneous solution phase together with a silicic acid ester such as tetraethyl orthosilicic acid ester (TEOS). The metal alkoxide has the problems of being expensive and requiring adjustment of the speed of a hydrolysis and condensation reaction with a silica precursor and thus being difficult in control of the reaction.

In addition, while odors of ammonia, acetic acid, acetaldehyde, and the like are known to be chemically adsorbed by silanol groups on a silica surface, the number of silanol groups per unit area is almost constant and therefore the specific surface area is needed to be increased for the purpose of an enhancement in odor elimination power per unit weight.

In introduction of a metal component into a synthesized porous material by a post-treatment (Japanese Patent Laid-Open No. 4-313348), a problem is that a metal is supported in a pore already completed, thereby causing a porous material to be small in specific surface area, pore volume and pore size.

Solution to Problem

The present invention provides a porous silica comprising a particle where a primary pore is formed, wherein the particle includes a metal containing substance having a particle size of 1 to 100 nm, and the specific surface area is 500 $m^2/g$ or more.

In addition, the present invention provides a deodorant comprising the porous silica.

Furthermore, the present invention provides a method for producing a porous silica, the method comprising:
  adding a fatty acid metal salt, a surfactant and a silica precursor to an aqueous solution, to assemble the silica precursor on a micelle structure surface where the fatty acid metal salt and the surfactant are mixed,
  adding a basic aqueous solution to a dispersion liquid, to mold a intermediate product, in which a silica wall is formed and the fatty acid metal salt is localized inside the silica wall;
  filtering and drying the precursor; and
  calcining the precursor to remove the surfactant in the micelle structure, to provide a porous silica comprising a metal containing substance derived from the fatty acid metal salt produced by heat of the calcination.

Advantageous Effects of Invention

The porous silica of the present invention can effectively eliminate odors of methylmercaptan, hydrogen sulfide, nonenal, and the like which are difficult to eliminate by a porous silica without a metal. The porous silica of the present invention not only has a large specific surface area and has many silanol groups on a silica surface, but also has a complicated pore structure including a primary pore and a secondary pore, and therefore exhibits high odor elimination speed and odor elimination capacity to odors of ammonia, trimethylamine, acetic acid, isovaleric acid and the like which are known to chemically adsorb to a silica surface.

BRIEF DESCRIPTION OF DRAWINGS

FIG. 12 is a graph representing particle size distribution measurement results.

DESCRIPTION OF EMBODIMENTS

First Embodiment

Figure 1:
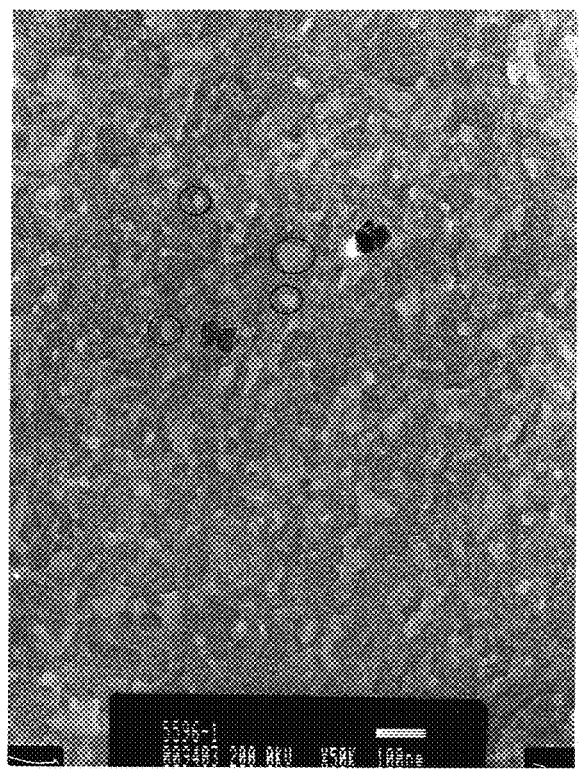
FIG. 1 illustrates a TEM image of the cross section in Example 1A-2.

A porous silica of a first embodiment is a porous silica comprising a particle where a primary pore is formed.

The primary pore of the particle is formed by self-assembly of a silica precursor in an aqueous solution by use of a fatty acid metal salt and a surfactant as templates. The primary pore is generally considered to have a pore size of 1 to 20 nm.

The surfactant is preferably a nonionic or cationic surfactant, more preferably an alkylammonium salt. The alkylammonium salt may be one having 8 or more carbon atoms, and is more preferably one having 12 to 18 carbon atoms in terms of industrial availability. Examples of the alkylammonium salt include cetyltrimethylammonium bromide, stearyltrimethylammonium bromide, cetyltrimethylammonium chloride, stearyltrimethylammonium chloride, dodecyltrimethylammonium bromide, octadecyltrimethylammonium bromide, dodecyltrimethylammonium chloride, octadecyltrimethylammonium chloride, didodecyldimethylammonium bromide, ditetradecyldimethylammonium bromide, didodecyldimethylammonium chloride and ditetradecyldimethylammonium chloride. These surfactants may be used singly or in combinations of two or more thereof. The concentration of the surfactant in the aqueous solution is preferably 50 to 400 mmol/L, more preferably 50 to 150 mmol/L. The surfactant serves as a molecular template which allows a micelle to be formed in water to thereby electrostatically accumulate the silica precursor on the surface thereof. The surfactant disappears by calcination, thereby forming the primary pore.

The fatty acid metal salt is preferably a fatty acid metal salt having 8 to 18 carbon atoms, more preferably a fatty acid metal salt having 12 to 18 carbon atoms. Examples of the fatty acid metal salt include an octanoic acid salt, a lauric acid salt and a stearic acid salt, but are not limited thereto. In addition, examples of the metal of the fatty acid metal salt include zinc, silver, nickel, copper, cobalt, manganese, cerium and zirconium. The metal is preferably zinc, silver, copper, manganese, and cobalt. These fatty acid metal salts may be used singly or in combinations of two or more thereof. The concentration of the fatty acid metal salt in the aqueous solution is preferably lower than the surfactant concentration, more preferably 0.2 to 5 mmol/L. The fatty acid metal salt is insoluble in water, and therefore is preferentially solubilized in the micelle interior serving as a hydrophobic environment. Therefore, the metal can be localized in the micelle interior, and a nanoparticle of a metal containing substance (metal complex) can be supported in a pore.

The silica precursor is preferably an alkoxysilane. An organic functional group on a silicon atom is lost by hydrolysis, and therefore has no effect on the structure of a synthesized product. If the organic functional group, however, is bulky, the hydrolysis speed is decreased to cause the synthesis time to be longer, and therefore examples of the silica precursor preferably include tetraethoxysilane, tetramethoxysilane, tetra-n-butoxysilane and sodium silicate. The silica precursor is more preferably tetraethoxysilane. These silica precursors may be used singly or in combinations of two or more thereof. The concentration of the silica precursor in the aqueous solution is preferably 0.2 to 1.8 mol/L, more preferably 0.2 to 0.9 mol/L. When sodium silicate is used as the silica precursor singly or in combination, a heating/refluxing operation in the aqueous solution at 200° C. or less for 20 to 2 hours is conducted. The silica precursor is subjected to hydrolysis (accelerated in an acidic or neutral condition), and thereafter connected by a dehydration condensation reaction (accelerated in a basic condition) to form a silica wall.

In the porous silica of the present embodiment, the particle includes a metal containing substance having a particle size of 1 to 100 nm. The particle size can be modulated by controlling the concentration of the fatty acid metal salt in the aqueous solution and a length of the carbon chain of the fatty acid.

In addition, in the porous silica of the present embodiment, the specific surface area is 500 $m^2/g$ or more. The specific surface area is preferably 1000 $m^2/g$ or more, more preferably 1200 $m^2/g$ or more. While odors of ammonia, acetic acid, acetaldehyde, and the like are known to be chemically adsorbed by silanol groups on a silica surface, the number of silanol groups per unit area is almost constant and therefore the specific surface area is needed to be increased for the purpose of an enhancement in odor elimination power per unit weight.

The porous silica of the present embodiment preferably has a secondary pore including a particle gap due to binding of the particles. The reason for this is because the presence of a coarse secondary pore can be expected to provide the effect of rapidly diffusing gas to the primary pore present inside, thereby leading to increases in odor elimination capacity and odor elimination speed.

The porous silica of the present embodiment can be used with being mixed with a resin. The porous silica of the present embodiment is formed from silica and a metal containing substance, and thus is high in heat resistance. Any conventionally known resin can be used as long as it is a thermoplastic resin which can be molten and molded, and examples can include olefin resins such as low-, moderate-, or high-density polyethylene, linear low-density polyethylene, linear ultralow-density polyethylene, isotactic polypropylene, syndiotactic polypropylene, a propylene-ethylene copolymer, polybutene-1, an ethylene-butene-1 copolymer, a propylene-butene-1 copolymer and an ethylene-propylene-butene-1 copolymer; polyester resins such as polyethylene terephthalate, polybutylene terephthalate and polyethylene naphthalate; polyamide resins such as nylon 6, nylon 6,6 and nylon 6,10; and polycarbonate resins. As the resin, polyethylene, polypropylene or polyester is particularly suitably used.

The porous silica of the present embodiment preferably has a lightness L* of 80 or more. When the lightness is high, the present porous silica can be less colored if used with being kneaded with the resin or the like, and it can be mixed with a pigment and thus colored so as to have a preferable color. When the present porous silica has a low lightness and can be liable to be colored, it can be inhibited from being colored by a reduction in the amount of the metal.

A deodorant of the present embodiment comprises the porous silica. The porous silica may be used with being mixed with a porous inorganic oxide. Examples of the porous inorganic oxide are aluminum and/or silicon oxides including zeolite, silica gel, alumina, sepiolite, spherical silica, pearlite, and activated carbon (mineral-based activated carbon or the like). The zeolite may be synthetic zeolite or natural zeolite (faujasite or the like). The porous silica has a heat resistance of 350° C. or more, and thus the porous inorganic oxide preferably has a heat resistance in the same temperature range so as not to cause an excellent heat resistance of the porous silica to be impaired.

The reason why the deodorant of the present embodiment exhibits excellent performance is presumed as follows.

The porous silica of the present embodiment serves as a deodorant moiety where a silanol group on a pore surface and a metal containing substance supported in the primary pore do not interfere with each other. The micelle structure including the fatty acid metal salt and the surfactant is used in order to form the intermediate product, thereby allowing the fatty acid metal salt to be localized inside the silica wall. The fatty acid metal salt is calcined to thereby allow the metal containing substance to be easily introduced in the primary pore. Basic, acidic and aldehyde-based odor components adsorb to silanol groups on the surface of the porous silica surface, and molecules (odor components) which adsorb are trapped in the primary pore due to capillary condensation. Furthermore, the aldehyde-based odor components are subjected to an oxidation decomposition reaction by the metal containing substance present inside. Such an odor elimination mechanism allows the deodorant of the present embodiment to be superior in odor elimination properties of mixed odors (Tables 2 and 3) or repeated odor elimination properties (Table 4) to respective deodorants obtained in a method of impregnating a porous silica with a metal solution described below (Example 1B-2) and a method of calcining a precursor obtained by using a water-soluble metal salt (Example 1B-3).

A method for producing a porous silica of the present embodiment comprises a step of adding a fatty acid metal salt, a surfactant and a silica precursor to an aqueous solution, to assemble the silica precursor on a micelle structure surface where the fatty acid metal salt and the surfactant are mixed. For example, the fatty acid metal salt and the surfactant are stirred and mixed at room temperature or more and 100° C. or less for 1 hour or more and 24 hours or less, and thereafter the silica precursor is added thereto, to thereby allow a mixed micelle of the fatty acid metal salt and the surfactant, and the silica precursor to be dispersed. The resultant is stirred at room temperature for additional 30 minutes or more, thereby providing a dispersion liquid where the silica precursor is assembled on the mixed micelle surface. The aqueous solution may also include an organic solvent such as ethanol or toluene, in addition to water.

The method for producing a porous silica of the present embodiment further comprises a step of adding a basic aqueous solution to a dispersion liquid, to mold a intermediate product. A silica wall is formed in the product, and the fatty acid metal salt is localized inside the silica wall.

Examples of the basic aqueous solution include respective aqueous solutions of sodium hydroxide, sodium carbonate, and ammonia. The basic aqueous solution is preferably an aqueous sodium hydroxide solution. These basic aqueous solutions may be used singly or in combinations of two or more thereof. The basic aqueous solution is added so that the pH of the dispersion liquid is preferably 8 to 14, more preferably 9 to 11. The base accelerates a dehydration condensation reaction of the silica precursor. The solution is rapidly made basic with the silica precursor being sufficiently hydrolyzed, thereby allowing the dehydration condensation reaction to occur at once. The surface tension of a condensation portion is thus increased to provide a spherical silica wall, and spherical bodies are jointed several times, thereby allowing spinodal decomposition (phase separation) to occur. The resulting structure is congealed by chemical crosslinking, to form a secondary pore.

The method for producing a porous silica of the present embodiment further comprises a step of filtering and drying the intermediate product. The filtration of the intermediate product is for example, by suction filtration and repeated rinsed with water until the pH of the filtrate reaches 7. The intermediate product is sufficiently dried by, for example, a drier or a vacuum drier.

The method for producing a porous silica of the present embodiment further comprises a step of calcining the intermediate product to remove the fatty acid and the surfactant in the micelle structure. The intermediate product is calcined at a temperature equal to or higher than the decomposition of the surfactant, preferably 500 to 600° C.

It is considered that a fatty acid metal is supported in the state of being encapsulated in the micelle of the surfactant, and therefore it is considered that, if the surfactant is allowed to disappear by calcination, the metal containing substance is preferentially exist inside the pore of the porous silica. The metal containing substance introduced can be thus expected to act effectively, and can be used not only in deodorant applications, but also in other industrial applications such as catalyst, separating agent and adsorbent applications. In addition, the metal containing substance can be encapsulated in a pore to thereby cover the original color of the metal containing substance with a white color of silica, thereby suppressing a reduction in lightness, generally caused in the case of introduction of a colored metal, and resulting in an excellent appearance of the deodorant.

The porous silica of the present embodiment is not spherical, and therefore, when kneaded with a resin, has difficulty in covering of the pore surface with the resin. The reason for this is because the presence of an uneven particle gap makes the resin unlikely to penetrate thereinto due to the maze effect. Therefore, a resin molded article obtained by kneading of the porous silica of the present embodiment can be expected to easily maintain the diffusion speed of odors to the deodorant, and to maintain the effect as the deodorant even after kneading of the resin.

Experimental Example 1

(Test Method)
(Specific Surface Area)

Measurement was made at a liquid nitrogen temperature according to a one-point method by use of FlowSorb 112300 Model manufactured by Micromeritics Instrument Corp.

(Color)

The lightness L* value was measured by use of an SM color computer (SM-4) manufactured by Suga Test Instruments Co., Ltd.

(Metal Content)

50 mg of a sample was accurately weighed, and dissolved in 5 ml of hydrochloric acid or nitric acid, and thereafter the metal concentration in the aqueous solution was measured by ICP-OES manufactured by Thermo Fisher Scientific Inc.

(Elimination Test of Various Odors)

Various odors were prepared in in an amount of 500 ml. The initial concentrations of ammonia, pyridine, trimethylamine, acetic acid, isovaleric acid, methylmercaptan, hydrogen sulfide, and acetaldehyde were 100 ppm, 12 ppm, 28 ppm, 30 ppm, 38 ppm, 8 ppm, 4 ppm, and 14 ppm, respectively. After 50 mg of a sample was placed therein and stirred for 30 minutes, the concentrations of various gases were measured by use of a gas detector tube manufactured by Gastec Corporation, and the odor elimination rate was calculated based on comparison with the initial concentration.

(Elimination Test of High-Concentration Acetaldehyde Odor)

Acetaldehyde at an initial concentration of 625 ppm was prepared in a 500-ml conical flask. After 100 mg of a sample was added thereto and stirred, the acetaldehyde concentration after 24 hours was measured by use of a gas detector tube manufactured by Gastec Corporation, and the odor elimination rate was calculated based on comparison with the initial concentration.

(Repeated Elimination Test of Acetaldehyde Odor)

A 500-ml conical flask in which 100 mg of a sample was placed was prepared. Preparation was made so that the acetaldehyde concentration in the flask was 700 ppm (Operation 1). The remaining acetaldehyde concentration after 24 hours was measured by use of a gas detector tube manufactured by Gastec Corporation (Operation 2), and ventilation was made for 1 hour (Operation 3). Operations 1 to 3 were repeated five times.

(TEM)

After being embedded with Quetol 812 (epoxy resin), the resultant was sliced into an ultrathin section by an ultramicrotome, and subjected to carbon vacuum vapor deposition and to measurement at 200 kV by use of JEM2010 manufactured by JOEL Ltd.

(Particle Size Distribution Measurement)

Measurement was made using Zetasizer Nano ZS manufactured by Malvern Instruments Ltd. The measurement was made using a disposable cell made of polystyrene with the RI of a dispersion medium (water), the RI of a sample, the viscosity, and the absorption rate of a sample being set to 1.330, 1.59, 0.8872, and 0.010, respectively, and the temperature being set to 25° C. The composition of a solution was as follows: (A) hexadecylammonium chloride:water:sodium hydroxide=0.225:125:0.225, (B) hexadecylammonium chloride:cobalt stearate:water:sodium hydroxide=0.225:0.0106:125:0.225, and (C) tetraethoxysilane:hexadecylammonium chloride:cobalt stearate:water:sodium hydroxide=1:0.225:0.0106:125:0.2725.

Example 1A-1

To a 300-ml beaker were added water, dodecyltrimethylammonium chloride and zinc stearate, and stirred at 100° C. for 1 hour to prepare an aqueous solution where zinc stearate was uniformly dispersed. After the resultant was cooled to room temperature, tetraethoxysilane was added and stirred until a uniform system was obtained. Next, an aqueous sodium hydroxide solution was added thereto, and stirred for 20 hours with a stirrer being rotated at 1000 rpm. The molar ratio in the mixed solution was tetraethoxysilane:dodecyltrimethylammonium chloride:zinc stearate:water:sodium hydroxide=1:0.225:0.0094:125:0.196; so that the amount of Zn in the synthesized product was 1 wt %. A solid product was filtered off from the resulting suspension, dried in vacuum at 80° C., and thereafter heated at 570° C. for 5 hours to remove an organic component. The evaluation results of the synthesized product are shown in Table 1. In addition, the results of the elimination test of various odors are shown in Table 2.

Example 1A-2

A synthesized product was obtained by the same method as in Example 1A-1 except that hexadecyltrimethylammonium chloride was used instead of dodecyltrimethylammonium chloride and manganese stearate was used instead of zinc stearate. The molar ratio in the mixed solution was tetraethoxysilane:hexadecyltrimethylammonium chloride:manganese stearate:water:sodium hydroxide=1:0.225:0.0111:125:0.225; so that the amount of Mn in the synthesized product was 1 wt %. The evaluation results of the synthesized product are shown in Table 1. In addition, the elimination performance of a methylmercaptan is shown in Table 2. In addition, a TEM image of the cross section is illustrated in FIG. 1. Particles having a uniform primary pore (white spot) having a size of 1 to 20 nm were observed. In addition, a secondary pore (where the epoxy resin appeared white (for example, portion surrounded by a circle)) including a particle gap was also included, and a metal containing substance particle (black portion) having a size of 1 to 100 nm was encapsulated. Herein, a metal containing substance particle having a size of 1 to 100 nm, as observed in the TEM image of the cross section, was not observed on the surface of the resulting synthesized product.

Example 1A-3

A synthesized product was obtained by the same method as in Example 1A-1 except that silver stearate was used instead of zinc stearate. The molar ratio in the mixed solution was tetraethoxysilane:dodecyltrimethylammonium chloride:silver stearate:water:sodium hydroxide=1:0.209:0.0057:125:0.225; so that the amount of Ag in the synthesized product was 1 wt %. The evaluation results of the synthesized product are shown in Table 1. In addition, the elimination performance of a methylmercaptan odor is shown in Table 2.

Example 1A-4

Figure 2:
FIG. 2 illustrates a TEM image of the cross section in Example 1A-4.
Figure 3:
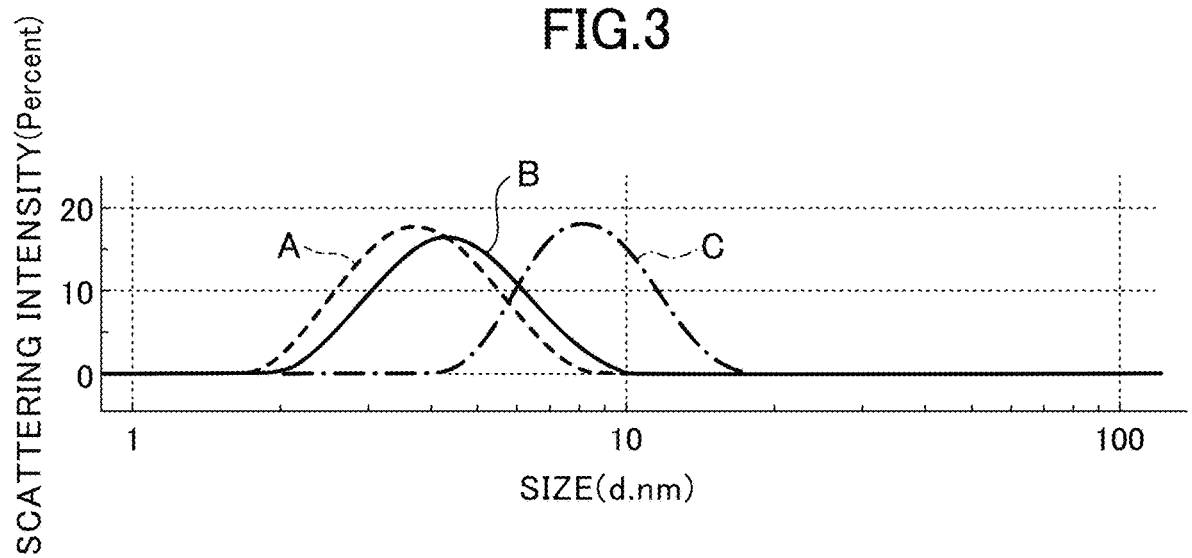
FIG. 3 illustrates particle size distribution measurement results.

A synthesized product was obtained by the same method as in Example 1A-1 except that hexadecyltrimethylammonium chloride was used instead of dodecyltrimethylammonium chloride and cobalt stearate was used instead of zinc stearate. The molar ratio in the mixed solution was tetraethoxysilane:hexadecyltrimethylammonium chloride:cobalt stearate:water:sodium hydroxide=1:0.225:0.0106:125:0.225; so that Co in the synthesized product was 1 wt %. The evaluation results of the synthesized product are shown in Table 1. In addition, the elimination performance of a high-concentration acetaldehyde odor is shown in Table 3, and the repeated elimination performance of an acetaldehyde odor is shown in Table 4. In addition, a TEM image of the cross section is illustrated in FIG. 2. The same structure as in FIG. 1 can also be confirmed in FIG. 2. In addition, the results of particle size distribution measurement at each stage of the synthesis are illustrated in FIG. 3. The ordinate axis represents the particle size of the micelle, and the abscissa axis represents the scattering intensity. That is, FIG. 3 illustrates the approximate existence probability. It was confirmed that the particle size became gradually larger in a case (B) where the fatty acid metal salt was further added and a case (C) where the alkoxysilane was further added as compared with a case (A) where only the surfactant was added. It could be thus confirmed that a micelle where the fatty acid metal was solubilized was formed and the silica precursor was assembled.

Example 1A-5

A synthesized product was obtained by the same method as in Example 1A-4 except that cobalt octanoate was used instead of cobalt stearate. The evaluation results of the synthesized product are shown in Table 1. In addition, the elimination performance of a high-concentration acetaldehyde odor is shown in Table 3.

Example 1A-6

To a 200-ml beaker water, hexadecyltrimethylammonium chloride and copper stearate, and stirred at 100° C. for 2 hours to prepare an aqueous solution where copper stearate was uniformly dispersed. Sodium silicate was added thereto over 20 minutes, and thereafter heated and refluxed at 200° C. for 30 minutes. After the resultant was cooled to room temperature, tetraethoxysilane was added and stirred until a uniform system was obtained. Next, an aqueous sodium hydroxide solution was added thereto, and stirred for 20 hours with a stirrer being rotated at 1000 rpm. The molar ratio in the mixed solution was tetraethoxysilane:sodium silicate:hexadecyltrimethylammonium chloride:copper stearate:water:sodium hydroxide=1:0.011:0.225:0.0009:125:0.196; so that the amount of Cu in the synthesized product was 0.1 wt %. A solid product was filtered off from the resulting suspension, dried in vacuum at 80° C., and thereafter heated at 570° C. for 5 hours to remove an organic component. The evaluation results of the synthesized product are shown in Table 1. In addition, the results of the elimination test of various odors are shown in Table 2.

Example 1B-1

The same synthesis method as in Example 1A-1 was performed except that no zinc stearate was added. The molar ratio in the mixed solution was tetraethoxysilane:dodecyltrimethylammonium chloride:water:sodium hydroxide=1:0.225:125:0.215. The evaluation results of the synthesized product are shown in Table 1. In addition, the results of the elimination test of various odors are shown in Table 2.

Example 1B-2

In a 100-ml beaker was prepared 5 ml of an aqueous 83 mmol/L cobalt nitrate solution, and 0.9 g of commercially available mesoporous silica (MSU-F produced by Sigma-Aldrich Co. LLC), dried in vacuum at 100° C., and thereafter calcined at 350° C. for 6 hours. The evaluation results of the synthesized product are shown in Table 1. In addition, the elimination performance of an acetaldehyde odor is shown in Table 3.

Example 1B-3

Synthesis was made based on Japanese Patent No. 4614196. Tetraethoxysilane was added to a 200-ml beaker and stirred with a stirrer being rotated at 600 rpm, and cobalt chloride dissolved in ethanol was added thereto. Next, octylamine was added thereto and stirred for 10 minutes, and thereafter an aqueous hydrochloric acid solution was added thereto and stirred for additional 1 hour as it was. The molar ratio of the mixed solution was tetraethoxysilane=octylamine:ethanol:cobalt chloride:hydrochloric acid:water=1:0.34:1.18:0.0105:0.034:38. A solid product was filtered off from the resulting suspension, dried in vacuum at 100° C., and thereafter heated at 600° C. for 1 hour to remove an organic component. The evaluation results of the synthesized product are shown in Table 1. In addition, the repeated elimination performance of an acetaldehyde odor is shown in Table 4.

Example 1B-4

A commercially available powder deodorant (KD411G produced by Rasa Industries, Ltd.) was evaluated. The evaluation results are shown in Table 1. In addition, the repeated elimination performance of an acetaldehyde odor is shown in Table 4.

TABLE 1

|  | Specific surface area [m$^2$/g] | Color (L*) | Metal content [wt %] | Metal particle size [nm] |
| --- | --- | --- | --- | --- |
| Example 1A-1 | 1321 | 92.9 | 1.03 | 20 |
| Example 1A-2 | 1116 | 44.96 | 1.05 | 20 |
| Example 1A-3 | 1338 | 88 | 1.00 | 20 |
| Example 1A-4 | 1178 | 66.92 | 1.01 | 20 |
| Example 1A-5 | 1235 | 64.8 | 0.66 | 20 |
| Example 1A-6 | 1299 | 88.8 | 0.08 | 20 |
| Example 1B-1 | 1005 | 88.07 | 0.00 | No particle |
| Example 1B-2 | 435 | 23.03 | 10.00 | 100 |
| Example 1B-3 | 1203 | 59.975 | 0.994 | No particle |
| Example 1B-4 | 252 | — | 9.05 | — |

TABLE 2

| | Odor elimination rate [%] | | | | | | | |
| --- | --- | --- | --- | --- | --- | --- | --- | --- |
| | Ammonia | Pyridine | Trimethylamine | Acetic acid | Isovaleric acid | Methylmercaptan | Hydrogen sulfide | Acetaldehyde |
| Example 1A-1 | 97 | 100 | 100 | 98 | 100 | 78 | 100 | 82 |
| Example 1A-2 | — | — | — | — | — | 100 | — | — |
| Example 1A-3 | — | — | — | — | — | 100 | — | — |
| Example 1A-6 | — | — | — | — | — | 100 | — | — |
| Example 1B-1 | 88 | 100 | 100 | 98 | 100 | 25 | 30 | 71 |

TABLE 3

| | Odor elimination rate [%] |
|---|---|
| Example 1A-4 | 100 |
| Example 1A-5 | 100 |
| Example 1B-1 | 61 |
| Example 1B-2 | 46 |

TABLE 4

| | Concentration of remaining acetaldehyde [ppm] | | | | | | | | | |
|---|---|---|---|---|---|---|---|---|---|---|
| | Day 1 | Day 2 | Day 3 | Day 4 | Day 5 | Day 6 | Day 7 | Day 8 | Day 9 | Day 10 |
| Example 1A-4 | 3 | 3 | 0 | 0 | 0 | 0 | 0 | 2 | 4 | 5 |
| Example 1B-3 | 18 | 12 | 20 | 4 | 4 | 1 | 1 | 4 | 8 | 10 |
| Example 1B-4 | 0 | 0 | 0 | 1 | 6 | 125 | 100 | 100 | 120 | 120 |

Second Embodiment

A porous silica is known to adsorb a basic odor such as an ammonia odor, an acidic odor such as an acetic acid odor, an acetaldehyde-based odor, and the like by means of a silanol group on the silica surface. According to findings by the present inventors, however, a basic odor and an acidic odor are strongly adsorbed to silica, but an acetaldehyde-based odor is relatively unlikely to be adsorbed thereto. The present embodiment is devised so that a porous silica, a deodorant, and a method for providing a porous silica, which have a high elimination power of an acetaldehyde-based odor, are obtained.

1. Porous Silica

A porous silica according to the second embodiment is a porous silica comprising a silica particle including a primary particle where a primary pore is formed, and a metal-containing particle supported on the silica particle.

The silica particle has a function of adsorbing a basic odor such as an ammonia odor, an acidic odor such as an acetic acid odor, an acetaldehyde-based odor, and the like by means of a silanol group formed on the surface thereof. The primary pore formed on the primary particle of the silica particle is considered to generally have a pore size of 1 to 20 nm. In addition, the silica particle preferably has a secondary pore including a particle gap due to binding of the primary particles. The reason for this is because the presence of a coarse secondary pore can be expected to provide the effect of rapidly diffusing gas to the primary pore present inside, thereby leading to increases in odor elimination capacity and odor elimination speed.

The metal-containing particle is supported on the porous silica in order to oxidatively decompose an acetaldehyde-based odor. The metal-containing particle can be supported on the porous silica, thereby oxidatively decomposing an acetaldehyde odor which is not completely adsorbed singly by a silica, to result in an increase in odor elimination ability. Herein, acetic acid generated by oxidative decomposition of acetaldehyde is adsorbed to a silanol group present on the surface of the silica particle, and the odor thereof is thus eliminated.

Examples of the metal of the metal-containing particle include at least one selected from the group consisting of zinc, silver, copper, manganese and cobalt, and cobalt is preferable.

The metal-containing particle has a particle size of less than 20 nm, preferably less than 15 nm, more preferably less than 10 nm. When the metal-containing particle has a smaller particle size, a higher catalyst efficiency can be achieved, thereby resulting in an increase in odor elimination performance. When a colored metal-containing particle is supported on the silica particle, coloration due to the metal-containing particle may impair the appearance of the porous silica. When the metal-containing particle has a small particle size, coloration of the porous silica can be less noticeable and the appearance is not impaired even if the metal-containing particle is colored.

Specifically, the lightness $L^*$ of the porous silica can be 50 or more, preferably 60 or more, according to the present embodiment. When the lightness is high, the present porous silica can be less colored if used with being kneaded with the resin or the like, and it can be mixed with a pigment and thus colored so as to have a preferable color. In addition, the saturation of the porous silica can be 17 or less, preferably 15 or less, according to the present embodiment.

The metal content in the porous silica is 0.5 wt % or more, preferably 0.6 wt % or more.

In addition, the metal particle rate of the porous silica is 70% or more, preferably 80% or more, more preferably 90% or more. The "metal particle rate" herein refers to the proportion of the mass of a metal supported, which is not doped into silica, to the mass of the entire metal included in the porous silica. In addition, the "doped" refers to a state where a metal is incorporated into the $SiO_4$ backbone of silica with a Si element being replaced with the metal.

According to findings by the present inventors, it is important for allowing the metal to exert the oxidative decomposition effect of acetaldehyde that the metal is supported in the form of a particle without being doped into the silica material. The metal content in the porous silica is 0.5 wt % or more and the metal particle rate is 70% or more, thereby resulting in a reduction in the content of a metal which is present in the form not contributing to the elimination ability of an acetaldehyde odor, and thus an enhancement in the ability as a deodorant.

In addition, in the porous silica of the present embodiment, the specific surface area is preferably 500 $m^2/g$ or more, more preferably 1000 $m^2/g$ or more. While odors of ammonia, acetic acid, acetaldehyde, and the like are known to be chemically adsorbed by silanol groups on a silica surface, the number of silanol groups per unit area is almost constant and therefore the specific surface area is needed to be increased for the purpose of an enhancement in odor elimination power per unit weight.

The porous silica of the present embodiment can be used with being mixed with a resin. The porous silica of the present embodiment is formed from silica and a metal containing substance, and thus is high in heat resistance. Any conventionally known resin can be used as long as it is a thermoplastic resin which can be molten and molded, and examples can include olefin resins such as low-, moderate-, or high-density polyethylene, linear low-density polyethylene, linear ultralow-density polyethylene, isotactic polypropylene, syndiotactic polypropylene, a propylene-ethylene copolymer, polybutene-1, an ethylene-butene-1 copolymer, a propylene-butene-1 copolymer and an ethylene-propylene-butene-1 copolymer; polyester resins such as polyethylene terephthalate, polybutylene terephthalate and polyethylene naphthalate; polyamide resins such as nylon 6, nylon 6,6 and nylon 6,10; and polycarbonate resins. As the resin, polyethylene, polypropylene or polyester is particularly suitably used.

The deodorant of the present embodiment comprises the porous silica. The porous silica may be used with being mixed with a porous inorganic oxide. Examples of the porous inorganic oxide are aluminum and/or silicon oxides including zeolite, silica gel, alumina, sepiolite, spherical silica, pearlite, and activated carbon (mineral-based activated carbon or the like). The zeolite may be synthetic zeolite or natural zeolite (faujasite or the like). Since the porous silica has a heat resistance of 350° C. or more, the porous inorganic oxide preferably has a heat resistance in the same temperature range so as not to cause an excellent heat resistance of the porous silica to be impaired.

2. Method for Producing Porous Silica

The present embodiment is also devised with respect to a method for providing the above porous silica. A production method described below can allow a porous silica being small in metal-containing particle size and having a high metal particle rate to be obtained.

Specifically, a production method according to the present embodiment comprises:

step (A) of mixing a surfactant, a metal salt and a ligand component in an aqueous solution, to produce a micelle containing a complex insoluble in water, in which the ligand component is coordinated to the metal of the metal salt, step (B) of adding a silica precursor to the aqueous solution after the step of producing a micelle, step (C) of adding a basic aqueous solution to the aqueous solution after the step of adding a silica precursor, step (D) of recovering the micelle (intermediate product) after the step of adding a basic aqueous solution, and step (E) of calcining the recovered the micelle to obtain a porous silica.

Hereinafter, the respective steps will be described in detail.

(A) Mixing of Surfactant, Metal Salt, and Ligand Component

First, a surfactant and a metal salt are mixed in an aqueous solution, to produce a micelle. The surfactant and the metal salt are mixed, to thereby produce a micelle containing the metal salt. For example, the metal salt and the surfactant can be stirred and mixed in water at room temperature or more and 200° C. or less for 30 minutes or more and 24 hours or less, to thereby form a micelle. The aqueous solution may also include an organic solvent such as ethanol or toluene, in addition to water.

The surfactant is preferably a nonionic or cationic surfactant, more preferably an alkylammonium salt. The alkylammonium salt may be one having 8 or more carbon atoms, and is more preferably one having 12 to 18 carbon atoms in terms of industrial availability. Examples of the alkylammonium salt include hexadecyltrimethylammonium chloride, cetyltrimethylammonium bromide, stearyltrimethylammonium bromide, cetyltrimethylammonium chloride, stearyltrimethylammonium chloride, dodecyltrimethylammonium bromide, octadecyltrimethylammonium bromide, dodecyltrimethylammonium chloride, octadecyltrimethylammonium chloride, didodecyldimethylammonium bromide, ditetradecyldimethylammonium bromide, didodecyldimethylammonium chloride and ditetradecyldimethylammonium chloride. These surfactants may be used singly or in combinations of two or more thereof. The concentration of the surfactant in the aqueous solution is preferably 50 to 400 mmol/L, more preferably 50 to 150 mmol/L. The surfactant serves as a molecular template which allows a micelle to be formed in water to thereby static electrostatically accumulate the silica precursor on its surface in a subsequent step. The surfactant finally disappears by calcination, thereby forming a primary pore.

The metal salt is a substance serving as the precursor of a metal. As the metal salt, for example, a fatty acid metal salt and a metal chloride can be used, and a fatty acid metal salt is preferable. The fatty acid metal salt is preferably a fatty acid metal salt having 8 to 24 carbon atoms, preferably 8 to 18, more preferably 12 to 18. The fatty acid metal salt is not particularly limited, examples thereof include an octanoic acid salt, a lauric acid salt and a stearic acid salt, and a stearic acid salt is preferable. These fatty acid metal salts may be used singly or in combinations of two or more thereof. The concentration of the fatty acid metal salt in the aqueous solution is preferably lower than the surfactant concentration, more preferably 0.2 to 5 mmol/L.

Herein, the concentration of the metal salt in the aqueous solution, and the type of the metal salt (the length of carbon chain or the like in the case of use of the fatty acid metal salt) can be controlled, and thus the particle size of a metal particle in a porous particle finally obtained can also be controlled.

Subsequently, a ligand component is added to the aqueous solution, thereby forming a complex insoluble in water, in which the ligand component is coordinated to the metal of the metal salt. It is considered that, when no ligand component is added, most of the metal included in the metal salt is present in the vicinity of the surface of a micelle. Alternatively, it is considered that, when the metal salt is a soluble salt such as cobalt chloride, the metal is hardly encapsulated into the micelle. On the contrary, when a ligand component is added to thereby form a complex insoluble in water, a complex formed is easily encapsulated into the micelle serving as a hydrophobic environment. That is, the metal present in the vicinity of the surface of the micelle can be moved into the micelle.

In addition, when the metal salt is a hydrophobic salt such as cobalt stearate, a ligand component can be added to thereby result in a reduction in the particle size of a micelle, and as a result, the particle size of a metal-containing particle included in a porous silica finally obtained can also be reduced.

In order to form the complex insoluble in water, for example, stirring and mixing may be made at room temperature or more and 200° C. or less for 30 minutes or more and 24 hours or less, after addition of the ligand component.

The ligand component is not particularly limited as long as it can form the complex insoluble in water together with the metal, and, for example, a compound having an 8-quinolinol structure is preferably used. Examples of the compound having an 8-quinolinol structure include 8-quinolinol (also referred to as oxine) and 5-(octyloxymethyl)-8-quinolinol.

As the ligand component, a substance is preferably used where complex formation constant of the-insoluble complex in which the ligand component is coordinated to the metal is larger than the complex formation constant of the metal salt. When the complex formation constant of the insoluble complex is larger than the complex formation constant of the metal salt, the ligand component can be easily coordinated to the metal, to promote formation of the insoluble complex. As a result, the amount of the complex encupsulated into the micelle can be increased.

For example, according to Basic Edition of Chemical Handbook, revised version 5, Maruzen (2004), the logarithm β1 and the logarithm β2 of the complex formation constant of oxine cobalt (complex of 8-quinolinol and cobalt) are 11.52 and 22.82, respectively. The numerical values of the complex formation constant of a complex of cobalt and 5-(octyloxymethyl)-8-quinolinol are considered to be the same as those of the complex of 8-quinolinol because 5-(octyloxymethyl)-8-quinolinol has a structure where an alkyl group is attached at the 5-position of 8-quinolinol and the alkyl group is positioned so as not to act as a coordinating group, thereby having no essential effect on the stability of metallic chelate.

Herein, the logarithm β1 of the complex formation constant of cobalt and acetic acid is 0.60. In addition, the logarithm β1 of the complex formation constant of cobalt stearate is considered to be comparable with that of acetic acid because the coordinating group is a carboxyl group.

The complex formation constant can be determined by measurement. The complex formation constant can be determined according to the following expressions by measuring the complex concentration $[ML_n^{(a-nb)+}]$ in the equilibrium condition, and the ion concentration $[M^{a+}]$ of a free metal and the concentration $[L^{b-}]$ of a free ligand.

$$M^{a+} + nL^{b-} \rightarrow ML_n^{(a-nb)+}$$

$$\beta_n = [ML_n^{(a-nb)+}]/[M^{a+}][L^{b-}]^n$$

Since the total concentration of the metal ion and the ligand is here kept constant in the measurement system, the concentrations of the complex and the free ligand, or the concentrations of the complex and the free metal ion are respectively in a dependent relationship, and two of such three variables may be measured as the concentrations or as physical amounts (absorbance of light, electric conductivity, optical rotation, and the like) in proportion to the concentrations.

The amount of the ligand component to be added is, for example, 2 to 5 molar equivalents, preferably 2 to 3 molar equivalents based on the metal of the metal salt.

Herein, the ligand component may be added to the aqueous solution at the same time as the addition of the surfactant and/or the metal salt. Preferably, however, the ligand component is added after the surfactant and the metal salt are mixed in the aqueous solution.

(B) Addition of Silica Precursor

Subsequently, a silica precursor is added to the aqueous solution. The silica precursor is added, and thus the silica precursor is assembled on the micelle surface.

The silica precursor is preferably an alkoxysilane. An organic functional group on a silicon atom is lost by hydrolysis, and therefore has no effect on the structure of a synthesized product. If the organic functional group, however, is bulky, the hydrolysis speed is decreased to cause the synthesis time to be longer, and therefore examples of the silica precursor preferably include tetraethoxysilane, tetramethoxysilane, tetra-n-butoxysilane and sodium silicate. The silica precursor is more preferably tetraethoxysilane. These silica precursors may be used singly or in combinations of two or more thereof. The concentration of the silica precursor in the aqueous solution is preferably 0.2 to 1.8 mol/L, more preferably 0.2 to 0.9 mol/L. When sodium silicate is used as the silica precursor singly or in combination, a heating/refluxing operation in the aqueous solution at 200° C. or less for 20 to 2 hours is conducted. The silica precursor is subjected to hydrolysis (accelerated in an acidic or neutral condition), and thereafter connected by a dehydration condensation reaction (accelerated in a basic condition) in step (D) described below, to form a silica wall.

(C) Addition of Basic Aqueous Solution

Subsequently, a basic aqueous solution is added. The basic aqueous solution is added, thereby dehydration-condensing the silica precursor accumulated on the micelle surface, to form a silica wall.

Examples of the basic aqueous solution include respective aqueous solutions of sodium hydroxide, sodium carbonate, and ammonia. The basic aqueous solution is preferably an aqueous sodium hydroxide solution. These basic aqueous solutions may be used singly or in combinations of two or more thereof. The basic aqueous solution is added so that the pH of the dispersion liquid is preferably 8 to 14, more preferably 9 to 11. The base accelerates a dehydration condensation reaction of the silica precursor. The solution is rapidly made basic with the silica precursor being sufficiently hydrolyzed, thereby allowing the dehydration condensation reaction to occur at once. The surface tension of a condensation portion is thus increased to provide a spherical silica wall, and spherical bodies are jointed several times, thereby allowing spinodal decomposition (phase separation) to occur. The resulting structure is congealed by chemical crosslinking, to form a secondary pore.

In this case, the complex encapsulated into the micelle is unlikely to be hydrolyzed and to be incorporated into the backbone of silica.

(D) Recovery of the Micelle

Subsequently, the micelle is recovered as an intermediate product. For example, the micelle can be filtered and dried, thereby recovering the intermediate product. The filtration of the micelle is for example, by suction filtration and repeated rinsed with water until the pH of the filtrate reaches 7. The micelle is sufficiently dried by, for example, a drier or a vacuum drier.

(E) Calcination

After recovery of the micelle, the intermediate product is calcined. The calcination removes an organic component included in the intermediate product. That is, the surfactant is removed, to form a porous silica having a pore. In addition, the organic component of the metal containing substance (complex) incorporated into the intermediate product is removed, and the metal-containing particle is supported in a pore of silica. Thus, a porous silica is obtained.

The calcination is conducted at a temperature equal to or higher than the decomposition temperature of the surfactant, preferably 400 to 600° C.

According to the above method, the ligand component can be added, to thereby convert the metal derived from the metal salt, to the complex insoluble in water, and encapsulated it into the micelle. As a result, if the metal component is supported in the state of being encapsulated in the micelle of the surfactant and the surfactant is allowed to disappear by calcination, the metal-containing particle can be preferentially distributed inside the pore of the porous silica with the metal being not incorporated into the $SiO_4$ backbone, thereby resulting in an increase in the metal particle rate. The metal introduced can be thus expected to act effectively, and can be used not only in deodorant applications, but also in other industrial applications such as catalyst, separating agent and adsorbent applications. In addition, the metal containing substance can be encapsulated in a pore to thereby cover the original color of the metal with a white color of silica, thereby suppressing a reduction in lightness, generally caused in the case of introduction of a colored metal, and resulting in an excellent appearance of the deodorant.

The porous silica of the present embodiment has a complicated structure where spherical bodies are jointed several times, and therefore, when kneaded with a resin, has difficulty in covering of the pore surface with the resin. The reason for this is because the presence of an uneven particle gap makes the resin unlikely to penetrate thereinto due to the maze effect. Therefore, a resin molded article obtained by kneading of the porous silica of the present embodiment can be expected to easily maintain the diffusion speed of odors to the deodorant, and to maintain the effect as the deodorant even after kneading of the resin.

In addition, according to the above method, the ligand component can be added, to thereby decrease the size of the micelle, and therefore the particle size of a metal particle finally obtained can also be decreased.

In addition, according to findings by the present inventors, the decomposition temperature of the complex produced by addition of the ligand component is lower than the decomposition temperature of the metal salt. As a result, organics can be removed from the metal containing substance in the intermediate product at a low calcination temperature in a short time.

Experimental Example 2

(Test Method)
(Specific Surface Area)
Measurement was made at a liquid nitrogen temperature according to a one-point method by use of FlowSorb 112300 Model manufactured by Micromeritics Instrument Corp.

(Color)
The $L^*$ value, the $a^*$ value and the $b^*$ value were measured by use of an SM color computer (SM-4) manufactured by Suga Test Instruments Co., Ltd. The lightness and the saturation were calculated as the $L^*$ value and $\sqrt{(a^{*2}+b^{*2})}$, respectively. A higher numerical value of the lightness expresses a white color. A smaller numerical value of the saturation expresses an achromatic color.

(Cobalt Content)
About 50 mg of the porous silica after calcination was accurately weighed, and dissolved in 4 ml of hydrochloric acid, and thereafter the metal concentration in the aqueous solution was measured by ICP-OES manufactured by Thermo Fisher Scientific Inc. It is considered that such a treatment with hydrochloric acid allows all of the cobalt component included in the porous silica, including a cobalt with which silica is doped, to be dissolved in hydrochloric acid. The total content of cobalt present in the porous silica was calculated as the cobalt content, based on the measurement results.

(Amount of Cobalt Particle)
After recovery (step E), about 0.5 g of the micelle before calcination (step F) was weighed, and washed with about 50 ml of ethanol in total 7 times. Thus, a component of cobalt included in the micelle, with which silica was not doped, was removed. A washing operation was performed 7 times, in which about 7 ml of ethanol was added to a sample and subjected to ultrasonic washing for 5 minutes, thereafter the solid content was precipitated by centrifuge, and the supernatant was disposed. Next, the solid content was dried in vacuum, and thereafter calcined at 570° C. for 5 hours, to obtain a porous silica. About 50 mg of the resulting sample was accurately weighed, and dissolved in 4 ml of hydrochloric acid, and thereafter the metal concentration in the aqueous solution was measured by ICP-OES manufactured by Thermo Fisher Scientific Inc. The "content of cobalt with which silica was doped" in the porous silica was calculated based on the measurement results. Furthermore, the content of cobalt with which silica was not doped, in the porous silica, was calculated as "the amount of the cobalt particle" according to the following expression.

Amount of cobalt particle=Content of cobalt−Content of cobalt with which silica was doped  (Expression 1):

(Cobalt Particle Rate)
The proportion of the mass of cobalt supported, with which silica was not doped, to the total mass of cobalt was calculated as the "cobalt particle rate" based on the measurement results of the cobalt content and the amount of the cobalt particle, according to the following expression.

Cobalt particle rate (%)=Amount of cobalt particle/Cobalt content×100  (Expression 2):

Herein, in Example 2B-1, cobalt was in the form of cobalt stearate and was difficult to extract with ethanol or water, and the amount thereof could not be quantitatively determined.

(Elimination Test of Acetaldehyde Odor)
Odor was prepared in 500 ml-flask. The initial concentration of acetaldehyde was set to 14 ppm or 750 ppm. In the odor was placed 50 mg of the porous silica and stirred for a constant time, and thereafter the concentration was measured with a gas detector tube 92L manufactured by Gastec Corporation, and was compared with the initial concentration to thereby calculate the odor elimination rate. Herein, the odor elimination test was performed with respect to the same sample twice in a condition where the initial concentration of acetaldehyde was set to 750 ppm, and the respective odor elimination rates at the first and second times were calculated.

(TEM)
The porous silica was embedded with Quetol 812 (epoxy resin), thereafter sliced into an ultrathin section by an ultramicrotome, and subjected to carbon vacuum vapor deposition and to measurement at 200 kV by use of JEM2010 manufactured by JOEL Ltd.

Example 2A-1

To a 300-ml beaker were added water, hexadecyltrimethylammonium chloride and cobalt stearate, and stirred at 100° C. for 1 hour to prepare an aqueous solution where cobalt stearate was uniformly dispersed. 8-Quinolinol was added thereto and stirred at 100° C. for additional 1 hour. After the resultant was cooled to room temperature, tetraethoxysilane was added and stirred until a uniform system was obtained. Next, an aqueous sodium hydroxide solution was added thereto, and stirred for 20 hours with a stirrer being rotated at 1000 rpm. The molar ratio in the mixed solution was tetraethoxysilane:hexadecyltrimethylammonium chloride:cobalt stearate:8-quinolinol:water:sodium hydroxide=1:0.225:0.0106:0.0319:125:0.225; so that the amount of Co in the synthesized product was 1 wt % and the ratio of 8-quinolinol to Co was 3 molar equivalents. A solid product was filtered off from the resulting suspension, dried in vacuum at 80° C., and thereafter calcined at 570° C. for 5 hours to remove an organic component.

Figure 4:
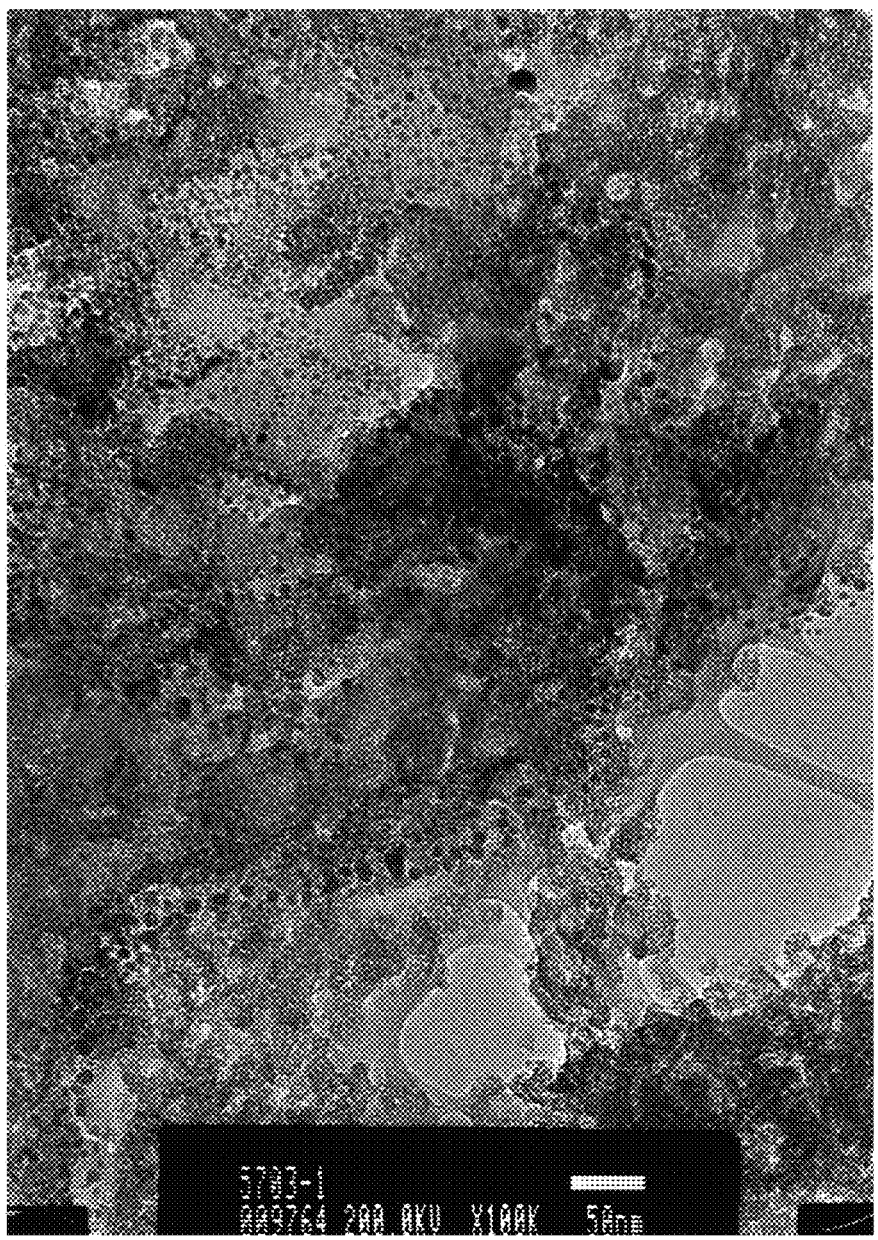
FIG. 4 illustrates a TEM image of a porous silica in Example 2A-1.

The evaluation results of the synthesized product are shown in Table 5. In addition, the results of the odor elimination test are shown in Table 6. In addition, a TEM image of the cross section is illustrated in FIG. 4. A structure was observed where a particle having a uniform primary pore (white spot) having a size of 1 to 20 nm was aggregated, as illustrated in FIG. 4. In addition, a metal particle (black portion) having a size of 5 to 10 nm was encapsulated. Herein, a metal particle having a size of about 5 nm, as observed in the TEM image of the cross section, was not observed on the surface of the resulting synthesized product.

Example 2A-2

The same synthesis method as in Example 2A-1 was performed except that 8-quinolinol was changed to 5-(octyloxymethyl)-8-quinolinol. The molar ratio in the mixed solution was tetraethoxysilane:hexadecyltrimethylammonium chloride:cobalt stearate:5-(octyloxymethyl)-8-quinolinol:water:sodium hydroxide=1:0.225:0.0106:0.0319:125:0.225; so that the amount of Co in the synthesized product was 1 wt % and the ratio of 5-(octyloxymethyl)-8-quinolinol to Co was 3 molar equivalents.

A solid product was filtered off from the resulting suspension, dried in vacuum at 80° C., and thereafter calcined at 570° C. for 5 hours to remove an organic component.

Figure 5:
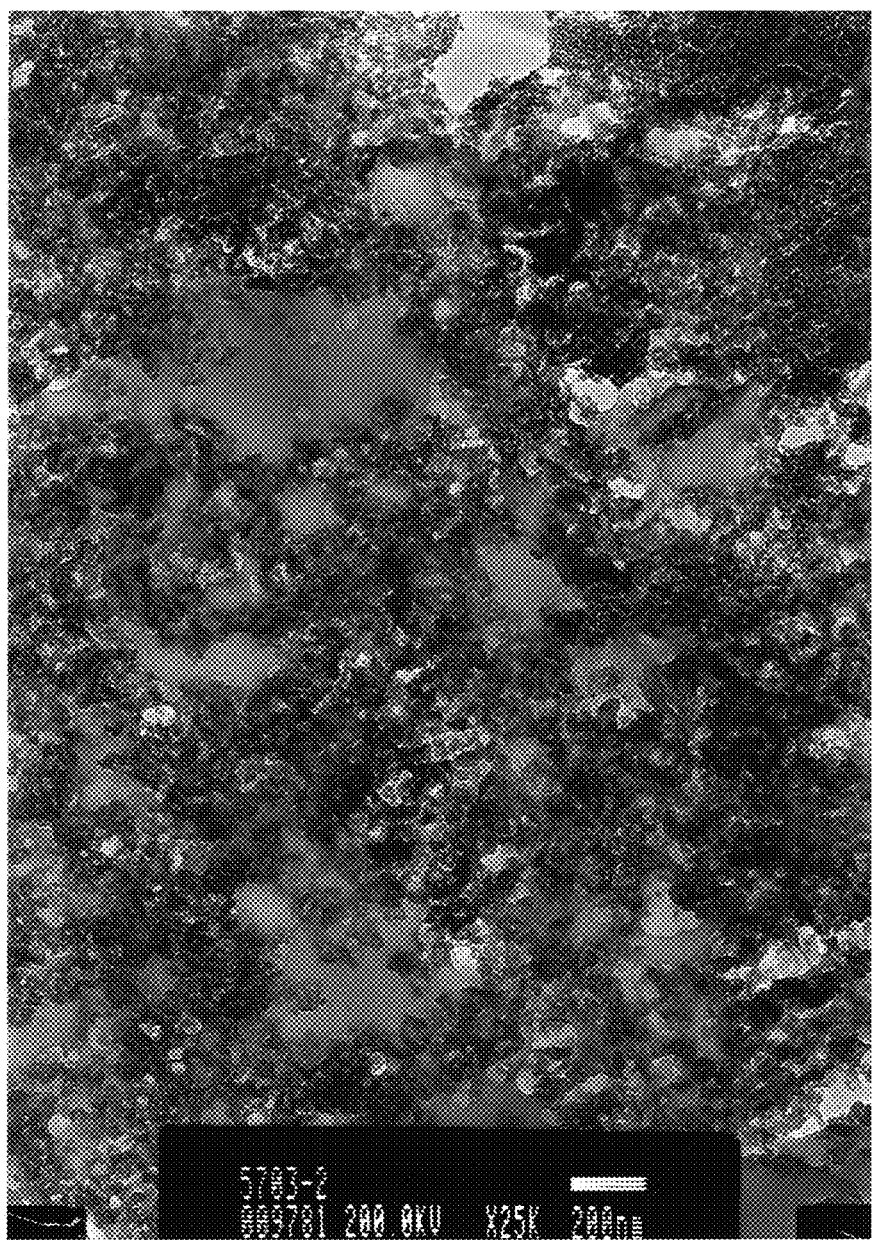
FIG. 5 illustrates a TEM image of a porous silica in Example 2A-2.

The evaluation results of the synthesized product are shown in Table 5. In addition, the results of the odor elimination test are shown in Table 6. In addition, a TEM image of the cross section is illustrated in FIG. 5. The same structure as in FIG. 4 can also be confirmed in FIG. 5.

Example 2A-3

The same synthesis method as in Example 2A-1 was performed except that cobalt stearate was changed to cobalt chloride. The molar ratio in the mixed solution was tetraethoxysilane:hexadecyltrimethylammonium chloride:cobalt chloride:8-quinolinol:water:sodium hydroxide=1:0.225:0.0106:0.0319:125:0.225; so that the amount of Co in the synthesized product was 1 wt % and the ratio of 8-quinolinol to Co was 3 molar equivalents. A solid product was filtered off from the resulting suspension, dried in vacuum at 80° C., and thereafter calcined at 570° C. for 5 hours to remove an organic component.

The evaluation results of the synthesized product are shown in Table 5. In addition, the results of the odor elimination test are shown in Table 6.

Example 2B-1

To a 300-ml beaker were added water, hexadecyltrimethylammonium chloride and cobalt stearate, and stirred at 100° C. for 1 hour to prepare an aqueous solution where cobalt stearate was uniformly dispersed. After the resultant was cooled to room temperature, tetraethoxysilane was added and stirred until a uniform system was obtained. Next, an aqueous sodium hydroxide solution was added thereto, and stirred for 20 hours with a stirrer being rotated at 1000 rpm. The molar ratio in the mixed solution was tetraethoxysilane hexadecyltrimethylammonium chloride cobalt stearate water sodium hydroxide=1:0.225:0.0106:125:0.225; so that the amount of Co in the synthesized product was 1 wt %. A solid product was filtered off from the resulting suspension, dried in vacuum at 80° C., and thereafter calcined at 570° C. for 5 hours to remove an organic component.

Figure 6:
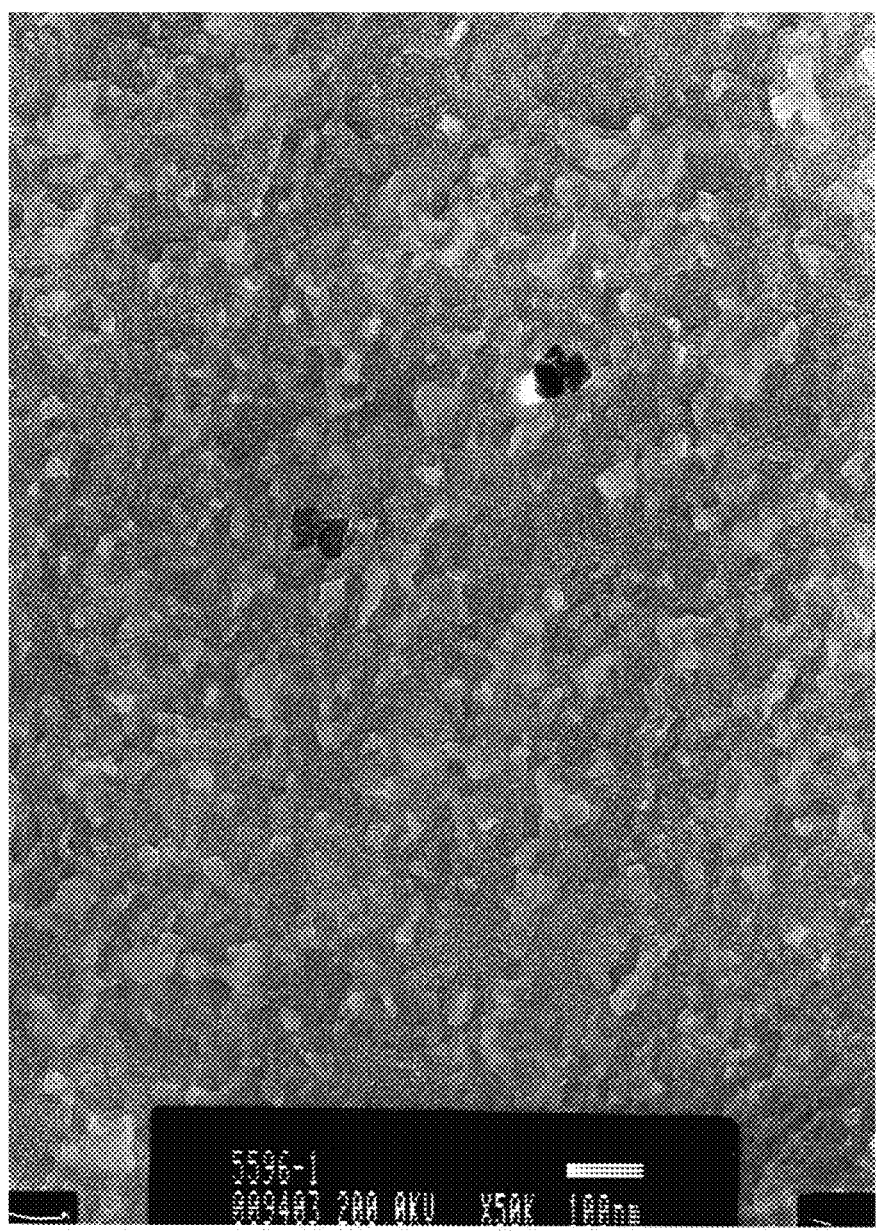
FIG. 6 illustrates a TEM image of a porous silica in Example 2B-1.

The evaluation results of the synthesized product are shown in Table 5. In addition, the results of the odor elimination test are shown in Table 6. In addition, a TEM image of the cross section is illustrated in FIG. 6. The same structure as in FIG. 4 can also be confirmed in FIG. 6. The amount of the particle, however, was small and the particle size was as large as about 20 nm, larger than that in Example 2A-1.

Example 2B-2

The same synthesis method as in Example 2B-1 was performed except that cobalt stearate was changed to oxine cobalt. The molar ratio in the mixed solution was tetraethoxysilane hexadecyltrimethylammonium chloride oxine cobalt water sodium hydroxide=1:0.225:0.0106:125:0.225; so that the amount of Co in the synthesized product was 1 wt %. A solid product was filtered off from the resulting suspension, dried in vacuum at 80° C., and thereafter calcined at 570° C. for 5 hours to remove an organic component.

Figure 7:
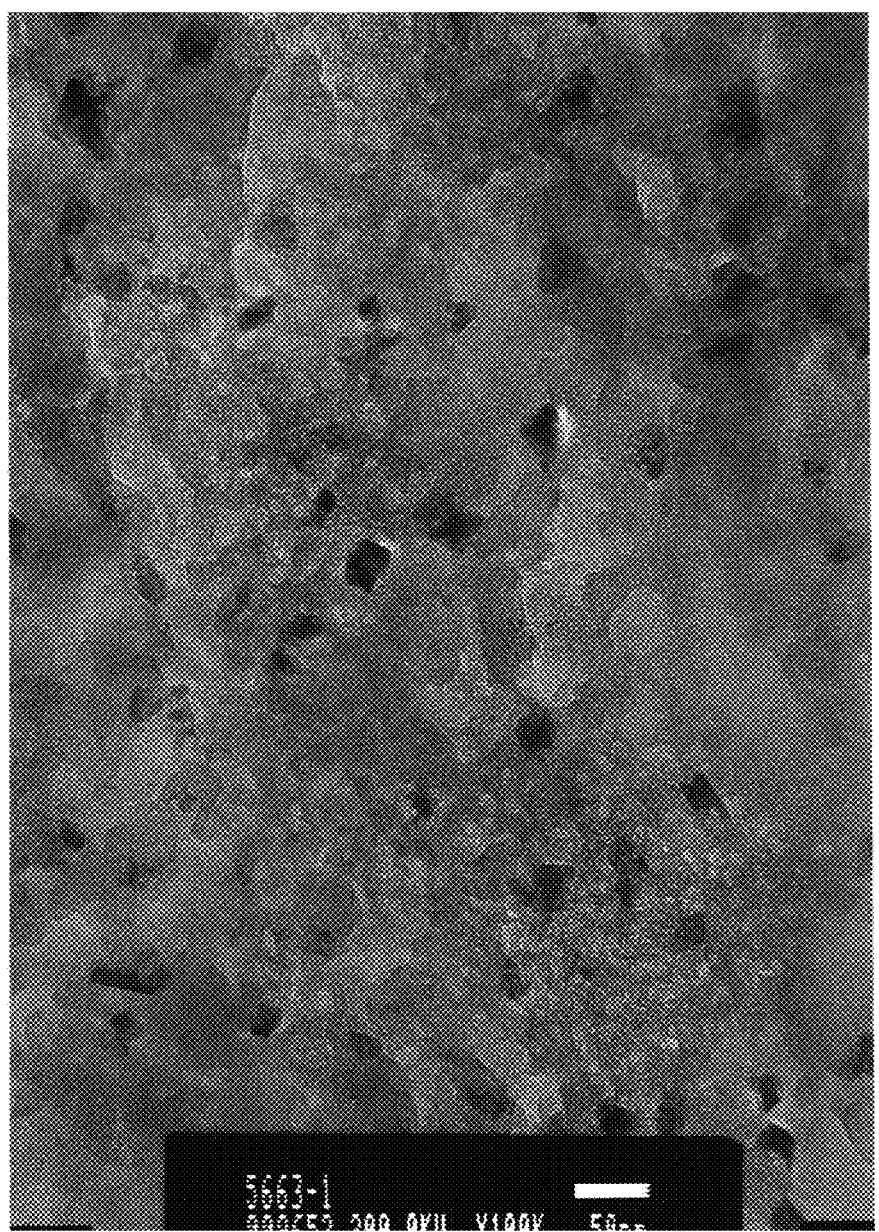
FIG. 7 illustrates a TEM image of a porous silica in Example 2B-2.

The evaluation results of the synthesized product are shown in Table 5. In addition, the results of the odor elimination test are shown in Table 6. Herein, the oxine cobalt was used which was obtained by preparing a solution of 8-quinolinol in ethanol and a solution of cobalt nitrate in water so that the ratio of the amounts of such substances was 2:1, heating/mixing the resultant at 50° C. for 10 minutes, then recovering a precipitate, and drying it at 130° C. In addition, a TEM image of the cross section is illustrated in FIG. 7. The same structure as in FIG. 4 can also be confirmed in FIG. 7. The particle size, however, was as large as about 20 nm, larger than that in Example 2A-1.

Example 2B-3

A sample after calcination was obtained by the same method as in Example 2B-1 except that no cobalt stearate was added. The molar ratio in the mixed solution was tetraethoxysilane hexadecyltrimethylammonium chloride water sodium hydroxide=1:0.225:125:0.225. In a 50-ml beaker was fractioned 0.396 g of the powder obtained by calcination, 0.4 ml of an aqueous 170 mmol/L cobalt nitrate solution and 8 ml of water were added thereto, and the resultant was dried in vacuum at 100° C. and thereafter calcined at 350° C. for 2 hours.

The evaluation results of the synthesized product are shown in Table 5. In addition, the results of the odor elimination test are shown in Table 6.

Example 2B-4

Synthesis was made based on Japanese Patent No. 4614196. Tetraethoxysilane was added into a 200-ml beaker and stirred with a stirrer being rotated at 600 rpm, and cobalt chloride dissolved in ethanol was added thereto. Next, octylamine was added thereto and stirred for 10 minutes, and thereafter an aqueous hydrochloric acid solution was added thereto and stirred for additional 1 hour as it was. The molar ratio of the mixed solution was tetraethoxysilane:octylamine:ethanol:cobalt chloride:hydrochloric acid:water=1:0.34=1.18:0.0105:0.034:38. A solid product was filtered off from the resulting suspension, dried in vacuum at 100° C., and thereafter calcined at 600° C. for 1 hour to remove an organic component.

Figure 8:
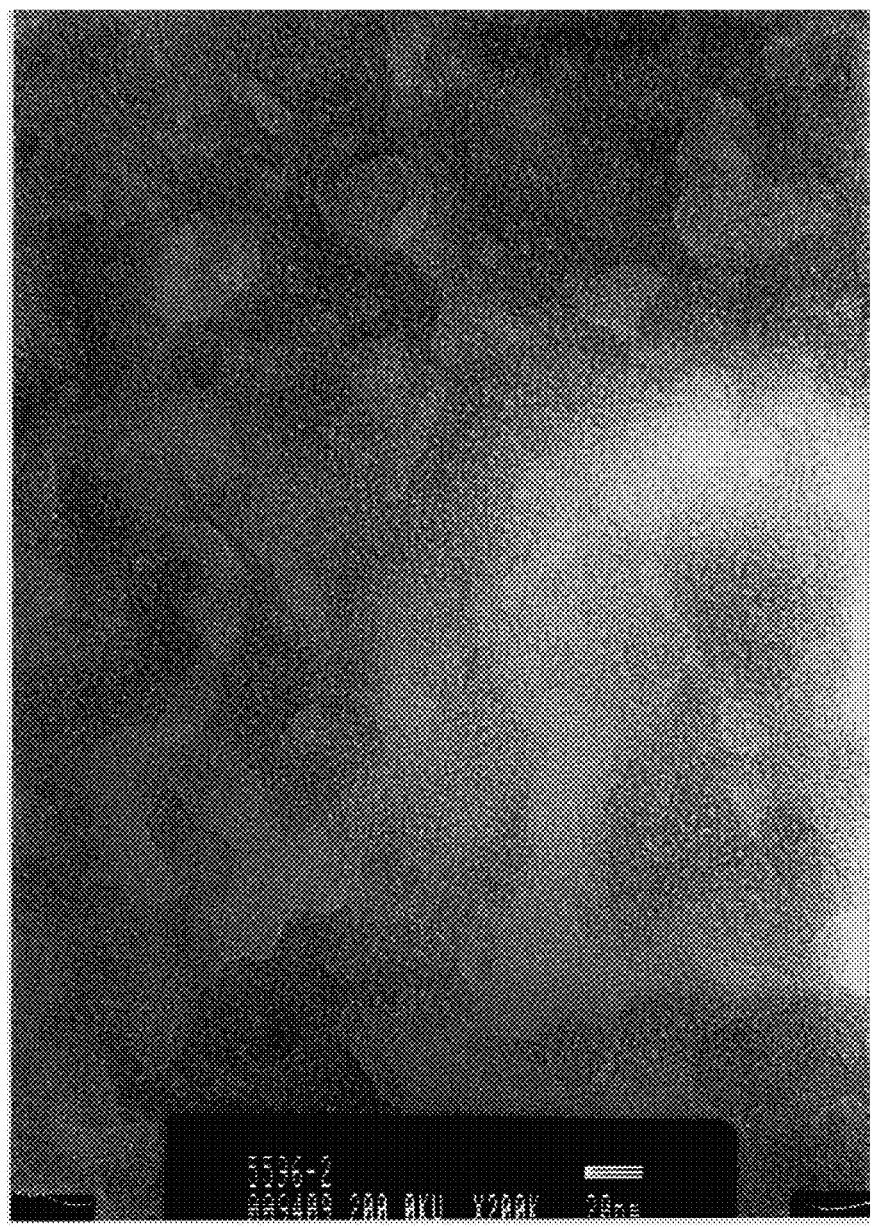
FIG. 8 illustrates a TEM image of a porous silica in Example 2B-4.

The evaluation results of the synthesized product are shown in Table 5. In addition, the results of the odor elimination test are shown in Table 6. In addition, a TEM image of the cross section is illustrated in FIG. 8. No particle was observed.

Example 2B-5

The same synthesis method as in Example 2B-1 was performed except that cobalt stearate was changed to cobalt chloride. The molar ratio in the mixed solution was tetraethoxysilane:hexadecyltrimethylammonium chloride:cobalt chloride:water:sodium hydroxide=1:0.225:0.0106:125: 0.225; so that the amount of Co in the synthesized product was 1 wt %. The evaluation results of the synthesized product are shown in Table 5. In addition, the results of the odor elimination test are shown in Table 6.

As shown in Table 5 and Table 6, Examples 2A-1 and 2A-2 exhibited a higher elimination performance of an acetaldehyde odor than, a lightness equal to or better than, and a lower saturation than Example 2B-1. In addition, a smaller metal particle size was also achieved. That is, it can be understood that the ligand component can be added to thereby allow a smaller metal particle size, and an enhanced elimination performance of an acetaldehyde odor without any reduction in lightness. In addition, the effect of addition of the ligand component was also verified by the following: Example 2A-3 exhibited a higher elimination performance of an acetaldehyde odor than, a lightness equal to or better than, and a lower saturation than Example 2B-5. Furthermore, Example 2A-3 exhibited an extremely higher cobalt particle rate than Example 2B-5. It has been thus found that addition of the ligand component enables cobalt in the form of a particle, with which silica is not doped, to be supported on silica.

In addition, Example 2B-2 exhibited a comparable elimination performance of an acetaldehyde odor with Examples 2A-1 to 2A-3. Example 2B-2, however, exhibited a lower metal particle rate, a larger metal particle size, and also a lower lightness than Examples 2A-1 and 2A-2. That is, it can be understood that, according to the method of the present embodiment, the metal salt and the ligand component can be added to thereby enhance the metal particle rate, reduce the metal particle size, and enhance the lightness, as compared with a case where no metal salt is used and the complex of the metal and the ligand component is directly mixed with the surfactant.

In Example 2B-3, an aqueous cobalt nitrate solution was used after calcination, to introduce cobalt, and therefore silica was not doped with cobalt and the metal particle rate was considered to be 100%. In Example 2B-3, however, the odor elimination performance was low in a low acetaldehyde concentration condition. In addition, the metal particle size was also large and the lightness was also low. It was considered that Example 2B-3 exhibited a large metal particle size, and thus a low catalyst efficiency and also a low odor elimination performance.

Example 2B-4 exhibited a lower odor elimination performance in a high-concentration acetaldehyde condition than Examples 2A-1 to 2A-3. The reason for this was considered that Example 2B-4 exhibited a low cobalt particle rate and was easily affected by poisoning of the catalyst.

TABLE 5

|  | Specific surface area | Co content [wt %] | Amount of Co particle [wt %] | Co particle rate [%] | Lightness | Saturation | Metal particle size [nm] |
|---|---|---|---|---|---|---|---|
| Example 2A-1 | 1140 | 0.88 | 0.87 | 98.9 | 65 | 11.9 | 5 |
| Example 2A-2 | 1126 | 0.88 | 0.88 | 99.9 | 73 | 16.6 | 5 |
| Example 2A-3 | 1416 | 1.35 | 1.23 | 90.7 | 64 | 10.4 | — |
| Example 2B-1 | 1178 | 1.02 | *1 | *1 | 65 | 17.9 | 20 |
| Example 2B-2 | 1189 | 1.01 | 0.84 | 64.5 | 44 | 9.2 | 20 |
| Example 2B-3 | 1186 | 0.91 | 0.91*2 | 100 | 36 | 7.0 | 25 |
| Example 2B-4 | 1196 | 0.99 | 0.36 | 36.1 | 60 | 19.7 | *3 |
| Example 2B-5 | 1201 | 1.03 | 0.008 | 0.83 | 60 | 14.2 | — |

*1 Cobalt stearate was not dissolved in water, ethanol, and the like, and therefore it was difficult to conduct an extraction test.
*2 Calculated in the assumption of Co content = Amount of particle.
*3 The presence of a particle could not be confirmed from TEM.

TABLE 6

Results of odor elimination test

|  | 14 ppm-30 min Humidity 50% | 750 ppm-24 h Humidity 50% | 750 ppm-24 h 2nd time |
|---|---|---|---|
| Example 2A-1 | 75 | 99.8 | 99.9 |
| Example 2A-2 | 66 | 99.8 | 99.3 |
| Example 2A-3 | 69 | 99.2 | 99.5 |
| Example 2B-1 | 62 | 99.0 | 98.7 |
| Example 2B-2 | 64 | 99.7 | 99.5 |
| Example 2B-3 | 57 | 98.0 | 96.0 |
| Example 2B-4 | 64 | 97.0 | 98.0 |
| Example 2B-5 | 57 | 99.2 | 99.0 |

(TG-DTA)

In addition, in Example 2A-1 and Example 2B-1, the sample before calcination was used to perform TG-DTA measurement. TGDTA 7220 manufactured by Hitachi High-Tech Science Corporation was used for the measurement. The measurement was performed in the measurement temperature range from 50 to 600° C. and at a rate of temperature rise of 2.5° C./min with air being allowed to flow at 100 ml/min.

Figure 9:
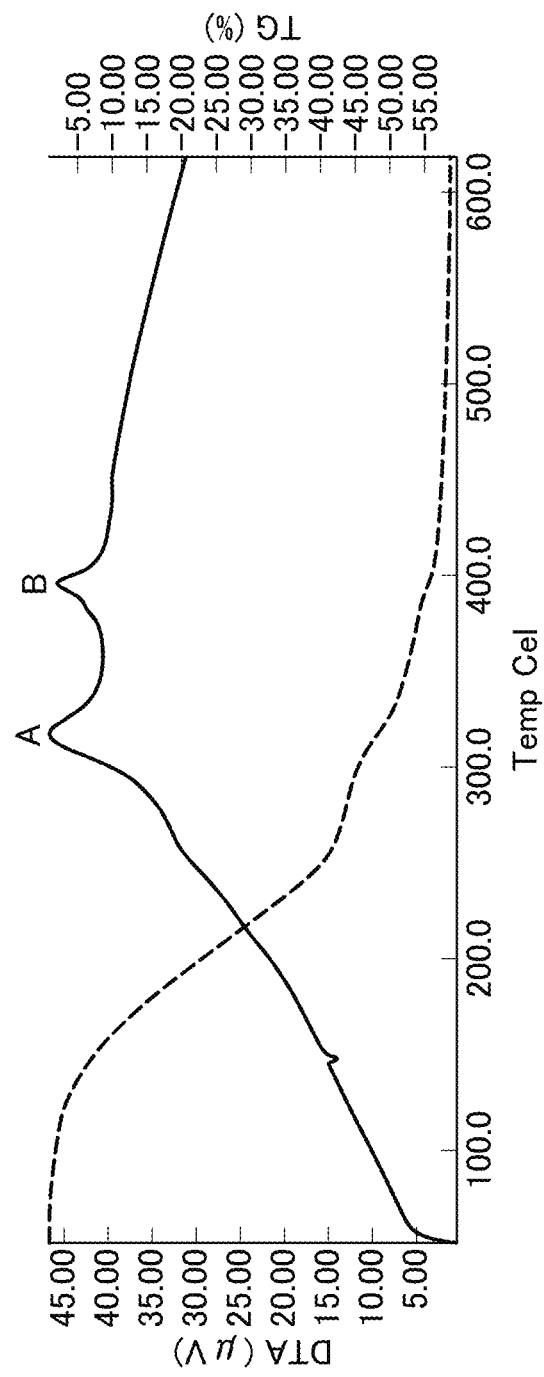
FIG. 9 is a graph representing TG-DTA measurement results of a precursor in Example 2A-1.
Figure 10:
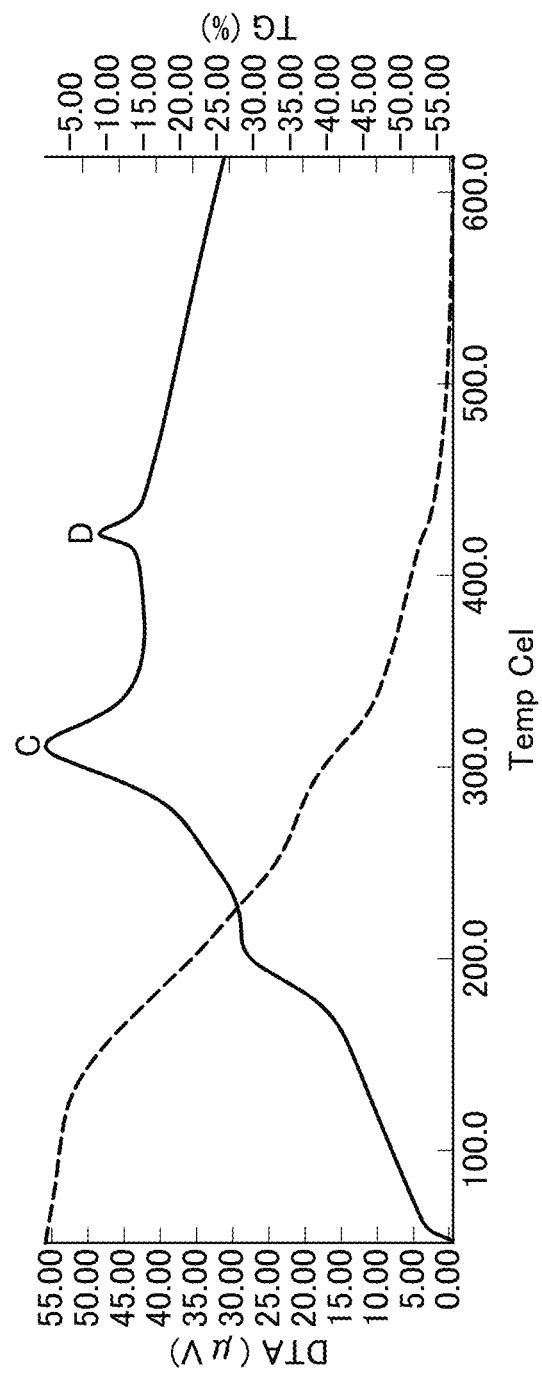
FIG. 10 is a graph representing TG-DTA measurement results of a precursor in Example 2B-1.

The results in Example 2A-1 are illustrated in FIG. 9, and the results in Example 2B-1 are illustrated in FIG. 10. In FIG. 9, peak A (313.8° C.) represents decomposition of the surfactant, and peak B (396.2° C.) represents decomposition of oxine cobalt (Co(ox)2) being a complex of cobalt and 8-quinolinol. On the other hand, in FIG. 10, peak C (311.4° C.) represents decomposition of the surfactant, and peak D (421.5° C.) represents decomposition of cobalt stearate (C18Co).

That is, not only a peak (311.4° C.) of the surfactant, but also a peak at a decomposition temperature of cobalt stearate (C18Co), of 421.5° C., was observed in Example 2B-1. On the contrary, no peak of cobalt stearate was observed, and a peak at a decomposition temperature (311.4° C.) of oxine cobalt $(Co(ox)_2)$ being a complex of cobalt and 8-quinolinol was observed in Example 2A-1. That is, it was found that 8-quinolinol was added to thereby coordinate cobalt derived from cobalt stearate, with 8-quinolinol, forming a complex.

In addition, the result indicated that cobalt stearate was converted to oxine cobalt lower in decomposition temperature. This indicated that the organic component could be removed from the cobalt-containing substance (complex) present in the intermediate product at a lower temperature during calcination in Example 2A-1.

(Particle Size Distribution Measurement)

Subsequently, in order to study the change in particle size due to addition of the ligand component, the following aqueous solutions (A) to (C) were prepared and particle size distribution measurement was performed using ELSZ-2000 manufactured by Otsuka Electronics Co., Ltd. The RI, the viscosity and the temperature of the dispersion medium (water) were set to 1.3328, 0.8878 and 25° C., respectively, and the measurement was performed using a quartz cell.

Aqueous solution (A): hexadecylammonium chloride:water=0.225:125

Aqueous solution (B): hexadecylammonium chloride:cobalt stearate:water=0.225:0.0106:125

Aqueous solution (C): hexadecylammonium chloride:cobalt stearate:water:8-quinolinol=0.225:0.0106:125:0.0319.

Figure 11:
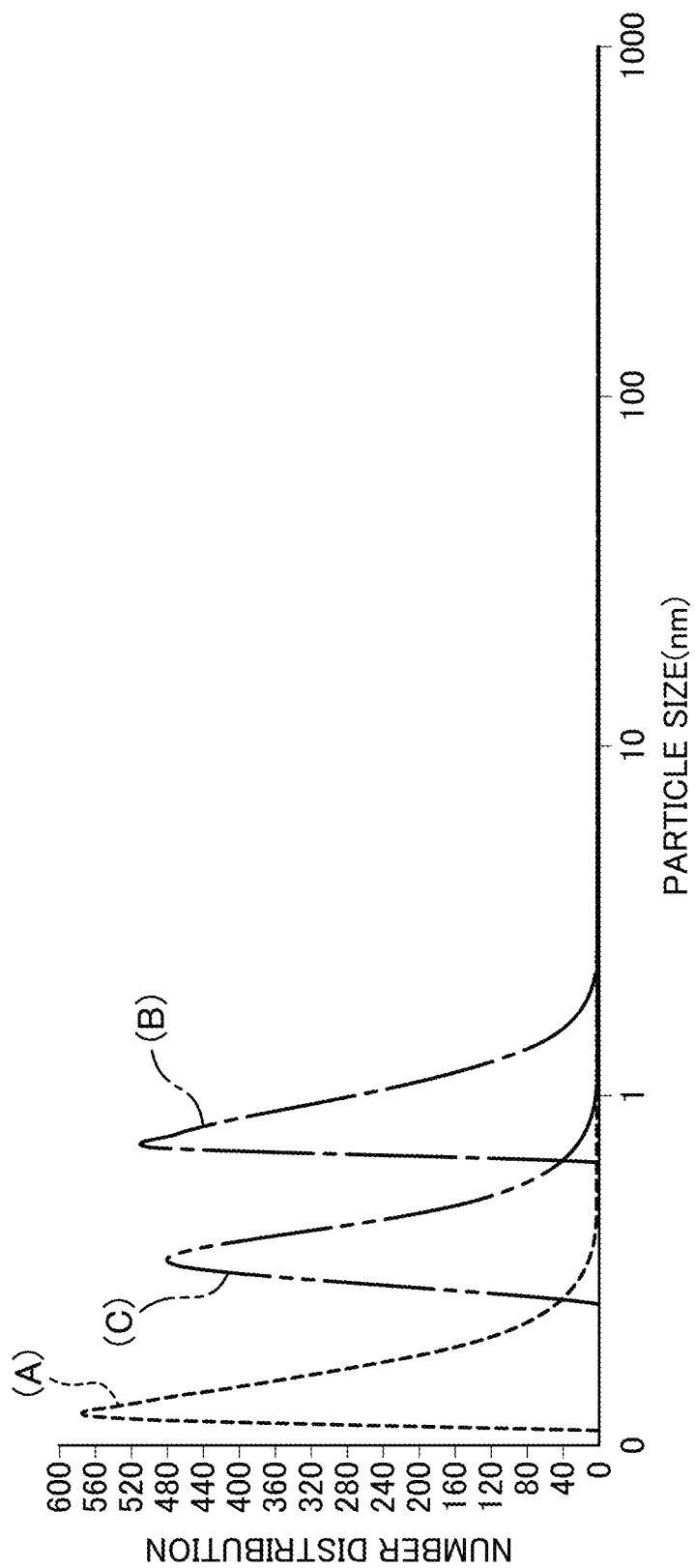
FIG. 11 is a graph representing particle size distribution measurement results.

FIG. 11 illustrates the results of the particle size distribution measurement. The average particle size of the micelle of aqueous solution (A) was 1.4 nm. The average particle size of the micelle of aqueous solution (B) was 143.7 nm. The average particle size of the micelle of aqueous solution (C) was 22.6 nm. It was confirmed from comparison of aqueous solutions (B) and (C) that 8-quinolinol was added to result in a significant reduction in the size of the micelle. This supposes that addition of 8-quinolinol can convert cobalt stearate to oxine cobalt, resulting in a smaller micelle to reduce the particle size of a metal particle in a porous silica finally obtained.

In addition, the same particle size distribution measurement was performed except that cobalt chloride was used instead of cobalt stearate. Specifically, the following aqueous solutions (D) and (E) were prepared, and the particle size distribution measurement was performed.

Aqueous solution (D); hexadecylammonium chloride:cobalt chloride:water=0.225:0.0106:125

Aqueous solution (E); hexadecylammonium chloride:cobalt chloride:water:8-quinolinol=0.225:0.0106:125:0.0319.

FIG. 12 illustrates the results of the particle size distribution measurement of aqueous solutions (A), (D) and (E). As previously described, the average particle size of the micelle of aqueous solution (A) was 1.4 nm. On the other hand, the average particle size of the micelle of aqueous solution (D) was 2.2 nm. The average particle size of the micelle of aqueous solution (E) was 25.3 nm. The average particle size of the micelle of aqueous solution (D) was almost the same as that of aqueous solution (A).

Since cobalt chloride is a soluble salt, it is considered that almost no cobalt in aqueous solution (D) is encapsulated into the micelle. On the contrary, the average particle size in aqueous solution (E) to which 8-quinolinol is added is larger. The reason for this is considered that addition of 8-quinolinol allows a complex insoluble in water to be formed and the cobalt component is thus encapsulated into the micelle, resulting in an increase in the average particle size of the micelle.

Third Embodiment

Subsequently, a third embodiment is described.

When a porous silica is used as a deodorant or the like, a desired color may be desired to be able to be given to the porous silica in terms of appearance. In order to be able to give a desired color to the porous silica, the porous silica desirably has a high degree of whiteness. When a metal-containing porous silica is adopted, however, the porous silica is sometimes colored by the metal component. On the contrary, the present embodiment is devised so that coloration by the metal component can be suppressed.

1. Porous silica. A porous silica of the present embodiment is a porous silica comprising a silica particle including a primary particle where a primary pore is formed, a first metal, and a second metal.

The silica particle has a function of adsorbing a basic odor such as an ammonia odor, an acidic odor such as an acetic acid odor, an acetaldehyde-based odor, and the like by means of a silanol group formed on the surface thereof. The primary pore formed on the primary particle of the silica particle is considered to generally have a pore size of 1 to 20 nm. The silica particle preferably also has a secondary pore including a particle gap due to binding of the primary particles. The reason for this is because the presence of a coarse secondary pore can be expected to provide the effect of rapidly diffusing gas to a primary pore present inside, thereby leading to increases in odor elimination capacity and odor elimination speed.

The first metal is contained in the porous silica in order to enhance odor elimination ability of the porous silica. The first metal is one or more selected from the group consisting of cobalt, zinc, silver, copper and manganese, and preferably includes cobalt.

According to findings by the present inventors, while the porous silica exhibits a high adsorption force with respect to a basic odor and an acidic odor, an acetaldehyde-based odor is relatively unlikely to be adsorbed by the porous silica. On the contrary, the first metal can be contained to thereby oxidatively decompose an acetaldehyde-based odor, resulting in an increase in odor elimination ability. Herein, acetic acid generated by oxidative decomposition of acetaldehyde is adsorbed by a silanol group present on the surface of the silica particle, and the odor thereof is thus eliminated.

The content of the first metal in the porous silica is preferably 0.5 wt % or more, more preferably 0.7 wt % or more.

In addition, at least a part of the first metal, with which silica is not doped, is preferably supported in the form of a particle (in the form of a metal oxide of the first metal) on the porous silica. The "doped" here refers to a state where a metal is incorporated into the $SiO_4$ backbone of silica with a Si element being replaced with the metal. If silica is doped with the first metal such as cobalt, silica is colored not to be able to obtain any porous silica high in the degree of whiteness.

In detail, the porous silica preferably has a first metal particle rate of 70% or more, more preferably 80% or more, further preferably 90% or more. The "first metal particle rate" herein refers to the proportion of the mass of the first metal supported on the silica particle without being doped therewith, to the mass of the entire first metal.

The particle size of the first metal particle is, for example, 1 to 100 nm.

The second metal is one or more selected from the group consisting of aluminum and zirconia, and preferably includes aluminum. The second metal can be contained in addition to the first metal, thereby suppressing coloration of the porous silica to obtain a porous silica higher in the degree of whiteness. Additionally, the second metal can be used to thereby enhance hydrothermal durability of the porous silica.

The content of the second metal in the porous silica is preferably 0.5 wt % or more, more preferably 1.0 wt % or more.

In addition, the silica particle is preferably doped with at least a part of the second metal. When the silica particle is doped with the second metal, hydrolysis of the siloxane bond of silica is suppressed to not easily break a pore structure, resulting in an enhancement in hydrothermal durability. Furthermore, when the silica particle is doped with the second metal, coloration of the porous silica is more suppressed. The reason for this is considered to be because the silica particle is doped with the second metal, thereby preventing diffusion of the first metal into silica to suppress coloration based on the first metal.

In detail, the porous silica preferably has a second metal particle rate of 0.5% or less, more preferably 0.3 wt % or less. The "second metal particle rate" herein refers to the proportion of the mass of the second metal supported on the silica particle without being doped therewith, to the mass of the entire second metal.

In addition, in the porous silica of the present embodiment, the specific surface area is preferably 500 $m^2/g$ or more, more preferably 1000 $m^2/g$ or more. While odors of ammonia, acetic acid, acetaldehyde, and the like are known to be chemically adsorbed by a silanol groups on a silica surface, the number of silanol groups per unit area is almost constant and therefore the specific surface area is needed to be increased for the purpose of an enhancement in odor elimination power per unit weight.

As described above, the porous silica of the present embodiment can contain the second metal, thereby suppressing coloration of the porous silica due to the first metal, to obtain a porous silica high in the degree of whiteness. In detail, the present embodiment can provide, for example, a porous silica having a lightness of 70 or more. When the lightness is high, the present porous silica can be less colored if used with being kneaded with the resin or the like, and it can be mixed with a pigment and thus colored so as to have a preferable color.

In addition, the present embodiment can provide, for example, a porous silica having a saturation of 10.0 or less, preferably 8.0 or less.

Furthermore, the present embodiment can contain the second metal, as described above, thereby providing a porous silica having a high hydrothermal durability. For example, the present embodiment can provide a porous silica having a specific surface area of 1000 $m^2/g$ or more after a hydrothermal treatment at 121° C. for 20 minutes.

The porous silica of the present embodiment can be used with being mixed with a resin. Any conventionally known resin can be used as long as it is a thermoplastic resin which can be molten and molded, and examples can include olefin resins such as low-, moderate-, or high-density polyethylene, linear low-density polyethylene, linear ultralow-density polyethylene, isotactic polypropylene, syndiotactic polypropylene, a propylene-ethylene copolymer, polybutene-1, an ethylene-butene-1 copolymer, a propylene-butene-1 copolymer and an ethylene-propylene-butene-1 copolymer; polyester resins such as polyethylene terephthalate, polybutylene terephthalate and polyethylene naphthalate; polyamide resins such as nylon 6, nylon 6,6 and nylon 6,10; and polycarbonate resins. As the resin, polyethylene, polypropylene or polyester is particularly suitably used.

The deodorant of the present embodiment comprises the porous silica. The porous silica may be used with being mixed with a porous inorganic oxide. Examples of the porous inorganic oxide are aluminum and/or silicon oxides including zeolite, silica gel, alumina, sepiolite, spherical silica, pearlite, and activated carbon (mineral-based activated carbon or the like). The zeolite may be synthetic zeolite or natural zeolite (faujasite or the like). Since the porous silica has a heat resistance of 350° C. or more, the porous inorganic oxide preferably has a heat resistance in the same temperature range so as not to cause an excellent heat resistance of the porous silica to be impaired.

2. Method for Producing Porous Silica

The method for producing a porous silica of the present embodiment comprises the following steps (A) to (D):
- step (A) of mixing a surfactant, a first metal salt, a second metal salt and a silica precursor in an aqueous solution, to form a micelle,
- step (B) of adding a basic aqueous solution to the aqueous solution after the step of forming a micelle,
- step (C) of recovering the micelle after the step of adding a basic aqueous solution, and
- step (D) of calcining the recovered micelle to obtain a porous silica.

Hereinafter, the respective steps will be described in detail.

(A) Mixing of Surfactant, First Metal Salt, Second Metal Salt and Silica Precursor First, a surfactant, a first metal salt, a second metal salt and a silica precursor are mixed in an aqueous solution, to form a micelle where the silica precursor is assembled on the surface. For example, the surfactant, the first metal salt and the second metal salt are stirred and mixed at room temperature or more and 200° C. or less, and thereafter the silica precursor is added. Thus, a mixed micelle of the surfactant, the first metal salt and the second metal salt, and the silica precursor are dispersed. These are stirred at room temperature for additional 30 minutes or more, thereby providing a dispersion liquid where the silica precursor is accumulated on the surface of the mixed micelle. The aqueous solution may also include an organic solvent such as ethanol or toluene, in addition to water.

The first metal salt is a substance serving as the precursor of a first metal. As the first metal salt, for example, a fatty acid metal salt or a metal chloride can be used, and a fatty acid metal salt is preferable. The fatty acid metal salt is preferably a fatty acid metal salt having 8 to 24 carbon atoms, preferably 8 to 18, more preferably 12 to 18. The fatty acid metal salt is not particularly limited, examples thereof include an octanoic acid salt, a lauric acid salt and a stearic acid salt, and a stearic acid salt is preferable. These fatty acid metal salts may be used singly or in combinations of two or more thereof. The concentration of the first metal salt in the aqueous solution is preferably lower than the surfactant concentration, more preferably 0.2 to 5 mmol/L.

Herein, the concentration of the first metal salt in the aqueous solution, and the type of the first metal salt (the length of carbon chain or the like in the case of use of the fatty acid metal salt) can be controlled, and thus the particle size of a first metal particle in a porous particle finally obtained can also be controlled.

The second metal salt is a substance serving as the source of a second metal. The second metal salt may be a water-soluble salt, and, for example, a chloride or a sulfate of the second metal is used.

The surfactant is preferably a nonionic or cationic surfactant, more preferably an alkylammonium salt. The alkylammonium salt may be one having 8 or more carbon atoms, and is more preferably one having 12 to 18 carbon atoms in terms of industrial availability. Examples of the alkylammonium salt include hexadecyltrimethylammonium chloride, cetyltrimethylammonium bromide, stearyltrimethylammonium bromide, cetyltrimethylammonium chloride, stearyltrimethylammonium chloride, dodecyltrimethylammonium bromide, octadecyltrimethylammonium bromide, dodecyltrimethylammonium chloride, octadecyltrimethylammonium chloride, didodecyldimethylammonium bromide, ditetradecyldimethylammonium bromide, didodecyldimethylammonium chloride and ditetradecyldimethylammonium chloride. These surfactants may be used singly or in combinations of two or more thereof. The concentration of the surfactant in the aqueous solution is preferably 50 to 400 mmol/L, more preferably 50 to 150 mmol/L. The surfactant serves as a molecular template which allows a micelle to be formed in water to thereby static electrostatically accumulate the silica precursor on its surface surfactant. The surfactant finally disappears by calcination, thereby forming a primary pore.

The silica precursor is preferably an alkoxysilane. An organic functional group on a silicon atom is lost by hydrolysis, and therefore has no effect on the structure of a synthesized product. If the organic functional group, however, is bulky, the hydrolysis speed is decreased to cause the synthesis time to be longer, and therefore examples of the silica precursor preferably include tetraethoxysilane, tetramethoxysilane, tetra-n-butoxysilane and sodium silicate. The silica precursor is more preferably tetraethoxysilane. These silica precursors may be used singly or in combinations of two or more thereof. The concentration of the silica precursor in the aqueous solution is preferably 0.2 to 1.8 mol/L, more preferably 0.2 to 0.9 mol/L. When sodium silicate is used as the silica precursor singly or in combination, a heating/refluxing operation in the aqueous solution at 200° C. or less for 20 to 2 hours is conducted. The silica precursor is subjected to hydrolysis (accelerated in an acidic or neutral condition), and thereafter connected by a dehydration condensation reaction (accelerated in a basic condition) in step (B) described below, to form a silica wall.

Herein, in the present step, a ligand component which is coordinated to the first metal to form a complex insoluble in water may also be further added. It is considered that, when the surfactant and the first metal salt are mixed to form a micelle, most of the metal included in the first metal salt is present in the vicinity of the surface of the micelle. On the contrary, when the ligand component is added to thereby form a complex insoluble in water, in which a coordination component is coordinated to the first metal, the complex formed is easily encapsulated into the micelle serving as a hydrophobic environment. That is, the first metal present in the vicinity of the micelle surface can be moved into the micelle. As a result, silica is unlikely to be doped with the first metal, and the particle rate of the first metal can be enhanced.

In addition, when the first metal salt is a fatty acid metal salt or the like, the fatty acid metal salt is hydrolyzed in the addition of a basic solution described below, and dehydration-condensed with Si, to thereby cause silica to be easily doped with the first metal. On the contrary, a complex insoluble in water can be formed, thereby preventing hydrolysis, and preventing silica from being doped with the first metal.

In addition, the ligand component can be added to thereby result in a reduction in the particle size of the micelle. As a result, the particle size of a first metal-containing particle included in a porous silica finally obtained can be reduced.

The ligand component is not particularly limited as long as it is coordinated to the first metal to form the complex insoluble in water, and, for example, a compound having an 8-quinolinol structure is preferably used. Examples of the compound having an 8-quinolinol structure include 8-quinolinol (also referred to as oxine) and 5-(octyloxymethyl)-8-quinolinol.

For example, according to Basic Edition of Chemical Handbook, revised version 5, Maruzen (2004), the logarithm β1 and the logarithm β2 of the complex formation constant of oxine cobalt (complex of 8-quinolinol and cobalt) are 11.52 and 22.82, respectively. The numerical values of the complex formation constant of a complex of cobalt and 5-(octyloxymethyl)-8-quinolinol are considered to be the same as those of the complex of 8-quinolinol because 5-(octyloxymethyl)-8-quinolinol has a structure where an alkyl group is attached at the 5-position of 8-quinolinol and the alkyl group is positioned so as not to act as a coordinating group, thereby having no essential effect on the stability of metallic chelate. Herein, the logarithm β 1 of the complex formation constant of cobalt and acetic acid is 0.60. In addition, the logarithm β1 of the complex formation constant of cobalt stearate is considered to be comparable with that of acetic acid because the coordinating group is a carboxyl group. The complex formation constant can be determined by measurement. The complex formation constant can be determined according to the following expressions by measuring the complex concentration $[ML_n^{(a-nb)+}]$ in the equilibrium condition, and the concentration $[M^{a+}]$ of a free metal ion and the concentration $[L^{b-}]$ of a free ligand.

$$M^{a+}+nL^{b-} \rightarrow ML_n^{(a-nb)+}$$

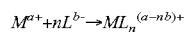

Since the total concentration of the metal ion and the ligand is here kept constant in the measurement system, the concentrations of the complex and the free ligand, or the concentrations of the complex and the free metal ion are each in a dependent relationship, and two of such three concentrations may be measured as the concentrations or as physical amounts (absorbance of light, electric conductivity, optical rotation, and the like) in proportion to the concentrations.

The amount of the ligand component to be added varies in the optimal range depending on the coordination number of the first metal ion. The amount is, for example, 1 to 2.5 molar equivalents, preferably 1 to 1.5 molar equivalents based on the coordination number of the first metal ion.

(B) Addition of Basic Aqueous Solution

Subsequently, a basic aqueous solution is added. The basic aqueous solution is added, thereby dehydration-condensing the silica precursor assembled on the micelle surface, to form a silica wall.

Examples of the basic aqueous solution include respective aqueous solutions of sodium hydroxide, sodium carbonate, and ammonia. The basic aqueous solution is preferably an aqueous sodium hydroxide solution. These basic aqueous solutions may be used singly or in combinations of two or more thereof. The basic aqueous solution is added so that the pH of the dispersion liquid is preferably 8 to 14, more preferably 9 to 11. The base accelerates a dehydration condensation reaction of the silica precursor. The solution is rapidly made basic with the silica precursor being sufficiently hydrolyzed, thereby allowing the dehydration condensation reaction to occur at once. The surface tension of a condensation portion is thus increased to provide a spherical silica wall, and spherical bodies are jointed several times, thereby allowing spinodal decomposition (phase separation) to occur. The resulting structure is congealed by chemical crosslinking, to form a secondary pore.

(E) Recovery of Micelle

Subsequently, the micelle is recovered as a intermediate product. For example, the micelle can be filtered and dried, thereby recovering a intermediate product. The filtration of the intermediate product is for example, by suction filtration and repeated rinsed with water until the pH of the filtrate reaches 7. The intermediate product is sufficiently dried by, for example, a drier or a vacuum drier.

(F) Calcination

After recovery of the micelle, the intermediate product is calcined. The calcination removes an organic component included in the intermediate product. That is, the surfactant is removed, to form a porous silica having a pore. The calcination is conducted at a temperature equal to or higher than the decomposition temperature of the surfactant, preferably 500 to 600° C.

The porous silica of the present embodiment has a complicated structure where spherical bodies are jointed several times, and therefore, when kneaded with a resin, has difficulty in covering of the pore surface with the resin. The reason for this is because the presence of an uneven particle gap makes the resin unlikely to penetrate thereinto due to the maze effect. Therefore, a resin molded article obtained by kneading of the porous silica of the present embodiment can be expected to easily maintain the diffusion speed of odors to the deodorant, and to maintain the effect as the deodorant even after kneading of the resin.

Experimental Example 3

(Test Method)
(Specific Surface Area)

Measurement was made at a liquid nitrogen temperature according to a one-point method by use of FlowSorb 112300 Model manufactured by Micromeritics Instrument Corp.

(Color)

The L* value, the a* value and the b* value were measured by use of an SM color computer (SM-4) manufactured by Suga Test Instruments Co., Ltd. The lightness and the saturation were calculated as the L* value and $\sqrt{(a^{*2}+b^{*2})}$, respectively.

(Metal Content)

About 50 mg of a sample was accurately weighed, and dissolved in 4 ml of hydrochloric acid, and thereafter the cobalt and aluminum concentrations in the aqueous solution were measured by ICP-OES manufactured by Thermo Fisher Scientific Inc. It is considered that such a treatment with hydrochloric acid allows all of cobalt and aluminum included in the porous silica, including any component (component with which silica is doped) incorporated into the backbone of silica, to be dissolved in hydrochloric acid. The total content of cobalt and the total content of aluminum present in the porous silica were calculated as the "cobalt content" and the "aluminum content", respectively, based on the measurement results.

(Metal Particle Rate)

About 0.5 g of a micelle (intermediate product) before calcination was weighed, and washed with about 50 ml of ethanol in total seven times. Each washing operation adopted corresponded to a procedure where about 7 ml of ethanol was added to a sample and subjected to ultrasonic washing for 5 minutes, thereafter the solid content was precipitated by centrifuge, and the supernatant was disposed. Thus, components of cobalt and aluminum included in the micelle, with which silica was not doped, were removed. Next, the solid content was dried in vacuum, and thereafter calcined at 570° C. for 5 hours, to obtain a porous silica.

About 50 mg of the resulting sample was accurately weighed, and dissolved in 4 ml of hydrochloric acid, and thereafter the cobalt and aluminum concentrations in the aqueous solution were measured by ICP-OES manufactured by Thermo Fisher Scientific Inc. The "content of cobalt with which silica was doped" and the "content of aluminum with which silica was doped", in the porous silica, were calculated based on the measurement results. Furthermore, the contents of cobalt and aluminum with which silica was not doped, in the porous silica, were calculated as "the amount of the cobalt particle" and "the amount of the aluminum particle", respectively, according to the following Expressions.

Amount of cobalt particle=Content of cobalt−Content of cobalt with which silica was doped  (Expression 1):

Amount of aluminum particle=Content of aluminum−Content of aluminum with which silica was doped  (Expression 2):

Furthermore, the cobalt particle rate and the aluminum particle rate were calculated according to the following Expressions.

Cobalt particle rate (%)=Amount of cobalt particle/Cobalt content×100  (Expression 3)

Aluminum particle rate (%)=Amount of aluminum particle/Aluminum content×100  (Expression 4)

(Elimination Test of Acetaldehyde Odor)

Prepared was 500 ml of an odor. The initial concentration of acetaldehyde was set to 750 ppm. Therein was placed 30 mg of a sample subjected to a hydrothermal treatment once, and stirred for 24 hours, and thereafter the remaining concentration of acetaldehyde was measured with a gas detector tube 92L, 92M or 92 manufactured by Gastec Corporation. In addition, the concentration of acetic acid was measured with a gas detector tube 81 manufactured by Gastec Corporation. Acetic acid was generated in an oxidative decomposition reaction of acetaldehyde, and the concentration of acetic acid measured here represents the concentration of acetic acid generated which could not be adsorbed by the sample. The odor elimination test was performed with respect to the same sample twice, and the respective remaining concentrations at the first and second times were measured.

(Hydrothermal Treatment)

About 0.1 g of a sample was weighed, and subjected to a hydrothermal treatment at 121° C. for 20 minutes by use of LSX-500 manufactured by Tomy Seiko Co., Ltd. The sample subjected to a hydrothermal treatment was dried at 160° C. for 2 hours before various measurements were performed.

Example 3A-1

To a 300-ml beaker were added water, hexadecyltrimethylammonium chloride, cobalt stearate and 8-quinolinol, and stirred to form a micelle. Thereafter, aluminum chloride was added thereto and stirred at 100° C. for 1 hour. After the resultant was cooled to room temperature, tetraethoxysilane was added and stirred until a uniform system was obtained. Next, an aqueous sodium hydroxide solution was added thereto, and stirred for 20 hours with a stirrer being rotated at 1000 rpm. The molar ratio in the mixed solution was tetraethoxysilane:hexadecyltrimethylammonium chloride:cobalt stearate 8-quinolinol:aluminum chloride:water:sodium hydroxide=1:0.225:0.0111:0.0332:0.0241:125:0.225;

so that the amounts of Co and Al in the synthesized product were each 1 wt % and the ratio of 8-quinolinol to Co was 3 molar equivalents. A solid product was filtered off from the resulting suspension, dried in vacuum at 80° C., and thereafter heated at 570° C. for 5 hours to remove an organic component.

Example 3A-2

The same synthesis method as in Example 3A-1 was performed except that cobalt stearate was changed to cobalt chloride. The molar ratio in the mixed solution was tetraethoxysilane:hexadecyltrimethylammonium chloride:cobalt chloride:8-quinolinol:aluminum chloride:water:sodium hydroxide=1:0.225:0.0111:0.0332:0.0241:125:0.225; so that the amounts of Co and Al in the synthesized product were each 1 wt % and the ratio of 8-quinolinol to Co was 3 molar equivalents.

Example 3A-3

The same synthesis method as in Example 3A-1 was performed except that no 8-quinolinol was added and heating and stirring for 1 hour thereafter were not performed. The molar ratio in the mixed solution was tetraethoxysilane:hexadecyltrimethylammonium chloride:cobalt stearate:aluminum chloride:water:sodium hydroxide=1:0.225:0.0111:0.0241:125:0.225; so that the amount of Co in the synthesized product was 1 wt %.

Example 3A-4

The same synthesis method as in Example 3A-2 was performed except that no 8-quinolinol was added and heating and stirring for 1 hour thereafter were not performed. The molar ratio in the mixed solution was tetraethoxysilane:hexadecyltrimethylammonium chloride:cobalt chloride:aluminum chloride:water:sodium hydroxide=1:0.225:0.0111:0.0241:125:0.225; so that the amount of Co in the synthesized product was 1 wt %.

Example 3B-1

Synthesis was made based on Japanese Patent No. 4614196. Tetraethoxysilane was added into a 200-ml beaker and stirred with a stirrer being rotated at 600 rpm, and cobalt chloride dissolved in ethanol was added thereto. Next, octylamine was added thereto and stirred for 10 minutes, and thereafter an aqueous hydrochloric acid solution was added thereto and stirred for additional 1 hour as it was. The molar ratio of the mixed solution was tetraethoxysilane:octylamine:ethanol:cobalt chloride:hydrochloric acid:water=1:0.34:1.18:0.0105:0.034:38. A solid product was filtered off from the resulting suspension, dried in vacuum at 100° C., and thereafter heated at 600° C. for 1 hour to remove an organic component.

Example 3B-2

The same synthesis method as in Example 3A-1 was performed except that no aluminum chloride was added and heating and stirring for 1 hour thereafter were not performed. The molar ratio in the mixed solution was tetraethoxysilane:hexadecyltrimethylammonium chloride:cobalt stearate:8-quinolinol:water:sodium hydroxide=1:0.225:0.0106:0.0319:125:0.225; so that the amount of Co in the synthesized product was 1 wt % and the ratio of 8-quinolinol to Co was 3 molar equivalents.

Example 3B-3

To a 300-ml beaker were added water and hexadecyltrimethylammonium chloride, and stirred at 100° C. for 1 hour to prepare an aqueous solution. After the resultant was cooled to room temperature, tetraethoxysilane was added and stirred until a uniform system was obtained. Next, an aqueous sodium hydroxide solution was added thereto, and stirred for 20 hours with a stirrer being rotated at 1000 rpm. The molar ratio in the mixed solution was tetraethoxysilane:hexadecyltrimethylammonium chloride:water:sodium hydroxide=1:0.225:125:0.225.

A solid product was filtered off from the resulting suspension, dried in vacuum at 80° C., and thereafter heated at 570° C. for 5 hours to remove an organic component.

Example 3B-4

The same synthesis method as in Example 3A-1 was performed except that neither cobalt stearate nor 8-quinolinol was added. The molar ratio in the mixed solution was tetraethoxysilane:hexadecyltrimethylammonium chloride:aluminum chloride:water:sodium hydroxide=1:0.225:0.0231:125:0.225. In a 50-ml beaker was fractioned 0.396 g of the powder obtained by calcination, 0.4 ml of an aqueous 170 mmol/L cobalt nitrate solution and 8 ml of water were added thereto, and the resultant was dried in vacuum at 100° C. and thereafter calcined at 350° C. for 2 hours.

Example 3B-5

The same synthesis method as in Example 3A-2 was performed except that neither 8-quinolinol nor aluminum chloride was added and heating and stirring for 1 hour thereafter were not performed. The molar ratio in the mixed solution was tetraethoxysilane:hexadecyltrimethylammonium chloride:cobalt chloride:water:sodium hydroxide=1:0.225:0.0106:125:0.225; so that the amount of Co in the synthesized product was 1 wt %.

Table 7 shows the measurement results of the specific surface area, the cobalt content, the cobalt particle rate, the aluminum content, the aluminum particle rate, the lightness and the saturation in each of Examples 3A-1 to 3A-4 and Examples 3B-1 to 3B-4.

In addition, Table 8 shows the measurement results of the specific surface area before and after the hydrothermal treatment.

Furthermore, Table 9 shows the measurement results of the elimination rate of an acetaldehyde odor after the hydrothermal treatment.

As shown in Table 7 and Table 9, Examples 3B-1, 3B-2 and 3B-5 each containing cobalt exhibited a lower remaining concentration of acetaldehyde, while exhibiting a lower lightness and a higher saturation, than Example 3B-3 not containing cobalt. That is, it can be understood that cobalt can be contained to thereby enhance the elimination performance of an acetaldehyde odor, but result in a decrease in lightness and an increase in saturation.

On the other hand, as shown in Table 7, Examples 3A-1 to 3A-4 exhibited a higher lightness and a lower saturation than Examples 3B-1, 3B-2 and 3B-5. That is, it can be understood that not only cobalt, but also aluminum can be contained in the porous silica to thereby suppress deterioration in hue due to use of cobalt being a colored metal.

The reason for this is considered to be because silica is doped with aluminum, thereby suppressing diffusion of a cobalt ion into silica not to cause any coloration due to a cobalt ion in Examples 3A-1 to 3A-4.

On the other hand, while the porous silica according to Example 3B-4 was good (low) in saturation, it could not achieve a desired lightness (70 or more).

In addition, while the porous silica according to each of Examples 3A-1 and 3A-2 had a high cobalt particle rate, it had an extremely low aluminum particle rate. That is, it can be understood that most of cobalt is supported in the form of a particle and silica is doped with most of aluminum. On the other hand, Examples 3A-3 and 3A-4, to which no ligand component was added, exhibited an extremely low cobalt particle rate as compared with Examples 3A-1 and 3A-2. That is, it has been found that addition of the ligand component results in an increase in the cobalt particle rate.

As shown in Table 8, the specific surface area was reduced according to each repetition of the hydrothermal treatment, in Examples 3B-1 to 3B-3, and Example 3B-5. On the contrary, the specific surface area was less reduced even repeating of the hydrothermal treatment and was kept at 1000 m$^2$/g or more in Examples 3A-1 to 3A-4. That is, it has been confirmed that aluminum is contained to enhance the hydrothermal durability. Herein, a reduction in the specific surface area was observed in each of Examples 3B-1 to 3B-3, and Example 3B-5. Therefore, it can be understood that a reduction in the specific surface area due to the hydrothermal treatment is not due to the presence of the cobalt particle.

As shown in Table 9, Examples 3A-1, 3A-2, 3A-3 and 3A-4 exhibited a lower remaining concentration of acetaldehyde after the hydrothermal treatment than Examples 3B-1 to 3B-5. That is, it can be understood that cobalt and aluminum can be contained in the porous silica to thereby enhance the odor elimination performance and also suppress deterioration in odor elimination performance due to the hydrothermal treatment.

TABLE 7

Identification results

| | Specific surface area | Co content [wt %] | Co particle rate [%] | Al content [wt %] | Al particle rate [%] | Lightness | Saturation |
|---|---|---|---|---|---|---|---|
| Example 3A-1 | 1067 | 0.89 | 99.6 | 1.17 | 0 | 83 | 6.8 |
| Example 3A-2 | 1373 | 1.07 | 97.3 | 1.29 | 0.15 | 73 | 6.1 |
| Example 3A-3 | 1273 | 0.76 | 6.1 | 1.22 | 0 | 82 | 7.7 |
| Example 3A-4 | 1351 | 0.76 | 5.8 | 1.20 | 0 | 82 | 7.6 |
| Example 3B-1 | 1196 | 0.99 | 36.1 | — | — | 60 | 19.7 |
| Example 3B-2 | 1140 | 0.88 | 98.9 | — | — | 65 | 11.9 |
| Example 3B-3 | 1307 | — | — | — | — | 88 | 2.9 |
| Example 3B-4 | 1434 | 0.91 | 0.91 | 1.22 | 0 | 68 | 2.2 |
| Example 3B-5 | 1201 | 1.03 | 0.83 | — | — | 60 | 14.2 |

TABLE 8

Change in specific surface area due to hydrothermal treatment

| | Before treatment | After one treatment | After two treatments |
|---|---|---|---|
| Example 3A-1 | 1067 | 1195 | 1141 |
| Example 3A-2 | 1373 | 1208 | 1068 |
| Example 3A-3 | 1273 | 1216 | 1229 |
| Example 3A-4 | 1351 | 1209 | 1224 |
| Example 3B-1 | 1196 | 966 | 713 |
| Example 3B-2 | 1140 | 707 | 575 |
| Example 3B-3 | 1307 | 863 | 626 |
| Example 3B-4 | 1434 | 1301 | 1210 |
| Example 3B-5 | 1201 | 726 | 621 |

TABLE 9

Remaining concentration in elimination test of acetaldehyde odor by use of sample after hydrothermal treatment

| | 1st time | | 2nd time | |
|---|---|---|---|---|
| | Acetaldehyde [ppm] | Acetic acid [ppm] | Acetaldehyde [ppm] | Acetic acid [ppm] |
| Example 3A-1 | 6 | 4 | 13 | 15 |
| Example 3A-2 | 4.5 | 6 | 11 | 22 |
| Example 3A-3 | 10 | 4.5 | 14 | 10 |
| Example 3A-4 | 10 | 4 | 13 | 10 |
| Example 3B-1 | 50 | 16 | 80 | 60 |
| Example 3B-2 | 11 | 8 | 24 | 32 |
| Example 3B-3 | 150 | 6 | 400 | 7 |
| Example 3B-4 | 11 | 5 | 15 | 12 |
| Example 3B-5 | 11 | 8 | 24 | 32 |

Still another aspect of the present invention may be as follows.

[1] A porous silica comprising a particle where a primary pore is formed, wherein the particle includes a metal containing substance having a particle size of 1 to 100 nm, and a specific surface area is 500 m$^2$/g or more.

[2] The porous silica according to [1], wherein the porous silica has a secondary pore including a particle gap due to binding of the particles.

[3] The porous silica according to [1] or [2], wherein a lightness L* is 80 or more.

[4] The porous silica according to any one of [1] to [3], wherein the particle is a particle where a primary pore is formed by arrangement of a silica precursor in an aqueous solution by use of a fatty acid metal salt and a surfactant as templates, and the metal containing substance is derived from the fatty acid metal salt.

[5] The porous silica according to [4], wherein the surfactant includes an alkylammonium salt.

[6] The porous silica according to [4] or [5], wherein a metal of the fatty acid metal salt is one or more selected from the group consisting of zinc, silver, copper, manganese and cobalt.

[7] A deodorant comprising the porous silica according to any one of the [1] to [6].

[8] A method for producing a porous silica, comprising:
adding a fatty acid metal salt, a surfactant and a silica precursor to an aqueous solution, to accumulate the silica precursor on a micelle structure surface where the fatty acid metal salt and the surfactant are mixed;
adding a basic aqueous solution to a dispersion liquid, to mold a intermediate product, in which a silica wall is formed and the fatty acid metal salt is localized inside the silica wall;
filtering and drying the intermediate product; and
calcining the precursor to remove the surfactant in the micelle structure, to provide a porous silica comprising a metal containing substance derived from the fatty acid metal salt produced by heat of the calcination.

Still another aspect of the present invention may be as follows.

[1] A method for producing a porous silica, comprising:
a step of mixing a surfactant, a metal salt and a ligand component in an aqueous solution, to produce a micelle containing a complex insoluble in water, in which the ligand component is coordinated to a metal of the metal salt,
a step of adding a silica precursor to the aqueous solution after the step of producing a micelle,
a step of adding a basic aqueous solution to the aqueous solution after the step of adding a silica precursor,
a step of recovering the micelle after the step of adding a basic aqueous solution, and
a step of calcining the recovered the micelle to provide a porous silica.

[2] The method for producing a porous silica according to [1], wherein a complex formation constant of the insoluble complex is larger than a complex formation constant of the metal salt.

[3] The method for producing a porous silica according to [1] or [2], wherein the metal of the metal salt is one or more selected from the group consisting of cobalt, zinc, silver, copper and manganese.

[4] The method for producing a porous silica according to any one of [1] to [3], wherein the metal salt is a fatty acid metal salt.

[5] The method for producing a porous silica according to any one of [1] to [4], wherein the metal salt is a metal chloride.

[6] The method for producing a porous silica according to any one of [1] to [5], wherein the ligand component is a compound having an 8-quinolinol structure.

[7] The method for producing a porous silica according to any one of [1] to [6], wherein the surfactant includes an alkylammonium salt.

[8] A porous silica comprising a silica particle including a primary particle where a primary pore is formed, and a cobalt-containing particle supported on the silica particle, wherein
a particle size of the cobalt-containing particle is less than 20 nm,
a cobalt content in the porous silica is 0.5 wt % or more, and
a cobalt particle rate is 70% or more.

[9] The porous silica according to [8], wherein the silica particle has a secondary pore including a particle gap due to binding of the primary particles.

[10] The porous silica according to [8] or [9], wherein a lightness is 50 or more.

[11] The porous silica according to any one of [8] to [10], wherein a saturation is 17 or less.

[12] A deodorant comprising the porous silica according to any one of [9] to [11].

Still another aspect of the present invention may be as follows.

[1] A porous silica comprising a silica particle including a primary particle where a primary pore is formed, cobalt, and aluminum, wherein a lightness is 70 or more.

[2] The porous silica according to [1], wherein the silica particle is doped with at least a part of aluminum.

[3] The porous silica according to [2], wherein
an aluminum content in the porous silica is 0.5 wt % or more,
an aluminum particle rate is 0.5% or less, and
the aluminum particle rate is a proportion of a mass of aluminum supported on the silica particle without being doped therewith, to a total mass of aluminum.

[4] The porous silica according to [1] or [2], wherein at least a part of cobalt is supported as a cobalt particle on the silica particle without being doped therewith.

[5] The porous silica according to [3], wherein
a cobalt content in the porous silica is 0.5 wt % or more,
a cobalt particle rate is 70% or more, and
the cobalt particle rate is a proportion of a mass of cobalt supported on the silica particle without being doped therewith, to a total mass of cobalt.

[6] The porous silica according to [3] or [4], wherein a particle size of the cobalt particle is 1 to 100 nm.

[7] The porous silica according to any one of [1] to [5], wherein a specific surface area after a hydrothermal treatment at 120° C. for 20 minutes is 1000 m$^2$/g or more.

[8] The porous silica according to any one of [1] to [6], wherein the silica particle has a secondary pore including a particle gap due to binding of the primary particles.

[9] A deodorant comprising the porous silica according to any one of [1] to [7].

The invention claimed is:

1. A porous silica comprising:
primary particles each of which has a primary pore with a primary pore size of 1 to 20 nm,
a secondary pore formed by a particle gap between the primary particles, and
a metal containing substance having a particle size of 1 to 100 nm,
wherein the porous silica has a specific surface area of 500 m$^2$/g or more,
wherein the metal containing substance is preferentially distributed and localized inside the pores of the porous silica without the metal being doped into a $SiO_4$ backbone,
wherein the metal containing substance is not present on the outer surface of the porous silica,
wherein the metal is cobalt,
wherein a metal particle rate is 70% or more,
the metal particle rate is a proportion of a mass of the metal inside the pores of the porous silica without being doped therewith, to a total mass of the metal,
wherein a silanol group is present on a pore surface,
wherein the porous silica further comprises aluminum,
an aluminum content in the porous silica is 1.0 wt % or more, an aluminum particle rate is 0.5% or less, and
the aluminum particle rate is a proportion of a mass of aluminum supported on the porous silica without being doped therewith, to a total mass of aluminum.

2. The porous silica according to claim 1, wherein the primary particle is a particle where a primary pore is formed by arrangement of a silica precursor in an aqueous solution by use of a fatty acid metal salt and a surfactant as templates, and the metal containing substance is derived from the fatty acid metal salt.

3. The porous silica according to claim 1, wherein a cobalt content in the porous silica is 0.5 wt % or more.

4. The porous silica according to claim 1, wherein a lightness of the porous silica is 70 or more.

5. The porous silica according to claim 4, wherein a specific surface area after a hydrothermal treatment at 120° C. for 20 minutes is 1000 $m^2/g$ or more.

6. A deodorant comprising the porous silica according to claim 1.

7. The porous silica according to claim 1, wherein a spherical silica wall is formed on the outer surface of the porous silica.

8. The porous silica according to claim 1, wherein the metal containing substance has a particle size of less than 20 nm.

* * * * *

UNITED STATES PATENT AND TRADEMARK OFFICE
CERTIFICATE OF CORRECTION

PATENT NO. : 11,090,403 B2
APPLICATION NO. : 15/745244
DATED : August 17, 2021
INVENTOR(S) : Kazuaki Ohashi et al.

It is certified that error appears in the above-identified patent and that said Letters Patent is hereby corrected as shown below:

In the Specification

At Column 7, Line 62, should read --...1:0.225:0.0106:125:0.225.--

Signed and Sealed this
Seventeenth Day of May, 2022

*Katherine Kelly Vidal*

Katherine Kelly Vidal
*Director of the United States Patent and Trademark Office*